United States Patent

Fey et al.

[11] Patent Number: 5,145,857
[45] Date of Patent: Sep. 8, 1992

[54] HMG-COA REDUCTASE-INHIBITING SUBSTITUTED AMINO-PYRIDINES

[75] Inventors: Peter Fey; Rolf Angerbauer; Walter Hübsch, all of Wuppertal; Thomas Philipps, Cologne; Hilmar Bischoff, Wuppertal; Dieter Petzinna, Duesseldorf; Delf Schmidt, Wuppertal, all of Fed. Rep. of Germany

[73] Assignee: Bayer Aktiengesellschaft, Leverkusen, Fed. Rep. of Germany

[21] Appl. No.: 568,442

[22] Filed: Aug. 15, 1990

[30] Foreign Application Priority Data

Sep. 6, 1989 [DE] Fed. Rep. of Germany ....... 3929507

[51] Int. Cl.$^5$ ............... C07D 213/75; C07D 401/04; A61K 31/445; A61K 31/44
[52] U.S. Cl. .................. 514/318; 514/343; 514/352; 514/353; 514/336; 546/194; 546/268; 546/281; 546/306; 546/309; 546/311; 546/312
[58] Field of Search ............... 546/194, 268, 281, 306, 546/309, 311, 312; 544/130, 131; 514/235.5, 318, 336, 343, 352, 353

[56] References Cited

U.S. PATENT DOCUMENTS

| | | | |
|---|---|---|---|
| 4,231,938 | 11/1980 | Monaghan et al. | 549/292 |
| 4,923,861 | 5/1990 | Picard et al. | 546/153 |
| 4,950,675 | 8/1990 | Chucholowski | 546/281 |
| 4,968,689 | 11/1990 | Angerbauer et al. | 514/277 |
| 5,006,530 | 4/1991 | Angerbauer et al. | 546/268 |

FOREIGN PATENT DOCUMENTS

| | | |
|---|---|---|
| 0306929 | 3/1989 | European Pat. Off. . |
| 0325129 | 7/1989 | European Pat. Off. . |
| 0325130 | 7/1989 | European Pat. Off. . |
| 3823045 | 1/1989 | Fed. Rep. of Germany ...... 546/268 |

Primary Examiner—Patricia L. Morris
Assistant Examiner—Lenora Miltenberger
Attorney, Agent, or Firm—Sprung Horn Kramer & Woods

[57] ABSTRACT

HMG-COA reductase-inhibiting compounds of the formula

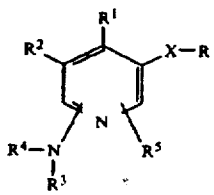
(I)

in which
X represents a group of the formula —CH$_2$—CH$_2$— or —CH=CH—,
R represents a group of the formula

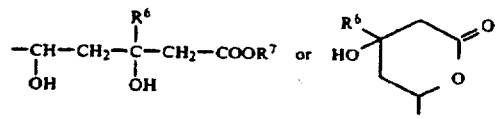

R$^1$ represents optionally substituted aryl,
R$^2$ represents —CH$_2$OR$^8$ or —X—R, and
R$^5$ represents straight-chain or branched alkyl having up to 10 carbon atoms, or and their pharmaceutically acceptable salts.

11 Claims, No Drawings

HMG-COA REDUCTASE-INHIBITING SUBSTITUTED AMINO-PYRIDINES

The invention relates to substituted aminopyridines, to intermediate compounds for their preparation, to their preparation and to their use in medicaments.

It is known that lactone derivatives isolated from fungal cultures are inhibitors of 3-hydroxy-3-methylglutaryl-coenzyme A reductase (HMG-CoA reductase) [mevinolin, EP 22,478; U.S. Pat. No. 4,231,938].

Pyridines and disubstituted pyridines having inhibitory action on HMG-CoA reductase are known from DOS (German Offenlegungsschrift) 3,801,406 and DOS 3,801,440.

Substituted amino-pyridines of the general formula (I)

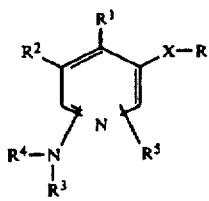

in which

X—represents a group of the formula —$CH_2$—$CH_2$— or —CH=CH—,

R—represents a group of the formula

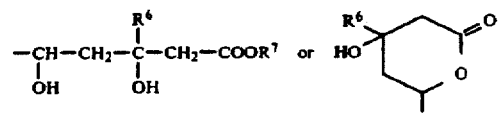

in which $R^6$ denotes hydrogen or straight-chain or branched alkyl having up to 10 carbon atoms and $R^7$ denotes hydrogen or straight-chain or branched alkyl having up to 10 carbon atoms, which may be substituted by phenyl, or denotes aryl having 6 to 10 carbon atoms, or a cation, $R^1$ represents aryl having 6 to 10 carbon atoms, which is optionally monosubstituted to tetrasubstituted by identical or different substituents from the series comprising straight-chain or branched alkyl, alkylthio, alkylsulphonyl, alkoxy or alkoxycarbonyl in each case having up to 8 carbon atoms, which may in turn be substituted by hydroxyl or phenyl, or by aryl, aryloxy, arylthio having 6 to 10 carbon atoms, benzyloxy, halogen, nitro, cyano, trifluoromethyl, trifluoromethoxy or benzyloxy, $R^2$ represents a group of the formula —$CH_2$—$OR^8$ or —X—R, in which $R^8$ denotes hydrogen, straight-chain or branched alkyl having up to 10 carbon atoms, which is optionally substituted by hydroxyl, halogen or phenyl, denotes aryl having 6 to 10 carbon atoms, or denotes a group of the formula —$COR^9$, in which $R^9$ denotes straight-chain or branched alkyl having up to 8 carbon atoms or phenyl, and X and R have the abovementioned meanings, $R^3$ and $R^4$ are identical or different and represent hydrogen, straight-chain or branched alkyl having up to 8 carbon atoms, phenyl or a group of the formula A—$R^{10}$, in which A denotes carbonyl or sulphonyl and $R^{10}$ denotes amino or alkoxy having up to 8 carbon atoms, straight-chain or branched alkyl having up to 8 carbon atoms or phenyl, which may in turn be substituted by hydroxyl, alkoxy having up to 8 carbon atoms or halogen, or denotes trifluoromethyl, or $R^3$ and $R^4$, together with the nitrogen atom, form a saturated or unsaturated 5- to 7-membered heterocycle having up to 3 heteroatoms from the series comprising nitrogen, sulphur or oxygen, and $R^5$ represents straight-chain or branched alkyl having up to 10 carbon atoms, or represents cycloalkyl having 3 to 8 carbon atoms, and their salts have now been found.

If $R^7$ forms an ester radical with the carboxyl group, a physiologically tolerable ester radical is preferably meant by this, which is easily hydrolyzed in vivo to give a free carboxyl group and a corresponding physiologically tolerable alcohol These include, for example, alkyl esters ($C_1$ to $C_6$) and aralkyl esters ($C_7$ to $C_{10}$), preferably ($C_1$-$C_4$)-alkyl esters and benzyl esters. Moreover, the following ester radicals may be mentioned: methyl esters, ethyl esters, propyl esters and benzyl esters.

If $R^7$ represents a cation, a physiologically tolerable metal cation or ammonium cation is preferably meant by this. Preferred cations in this connection are alkali metal cations or alkaline earth metal cations such as, for example, sodium, potassium, magnesium or calcium cations, and also aluminum or ammonium cations, as well as non-toxic substituted ammonium cations formed from amines such as ($C_1$-$C_4$)-dialkylamines, ($C_1$-$C_4$)-trialkylamines, procaine, dibenzylamine, N,N'-dibenzylethylenediamine, N-benzyl-$\beta$-phenylethylamine, N-methylmorpholine or N-ethylmorpholine, 1-ephenamine, dihydroabietylamine, N,N'-bis-dihydroabietylethylenediamine, N-lower alkylpiperidine and other amines which can be used for the formation of salts.

Surprisingly, the substituted amino-pyridines according to the invention show a superior inhibitory action on a HMG-CoA reductase (3-hydroxy-3-methylglutaryl-coenzyme A reductase).

Preferred compounds of the general formula (I) are those in which

X represents a group of the formula —$CH_2$—$CH_2$— or —CH=CH—,

R represents a group of the formula

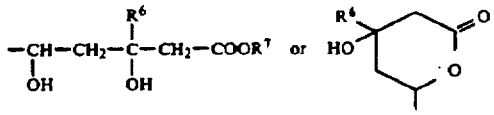

in which $R^6$ denotes hydrogen or straight-chain or branched alkyl having up to 8 carbon atoms and $R^7$ denotes hydrogen or straight-chain or branched alkyl having up to 8 carbon atoms, or benzyl, or denotes phenyl or a cation, $R^1$ represents phenyl which is optionally monosubstituted to trisubstituted by identical or different substituents from the series comprising straight-chain or branched alkyl, alkoxy or alkoxycarbonyl in each case having up to 6 carbon atoms, which may in turn be substituted by phenyl, or is substituted by phenyl, phenoxy, fluorine, chlorine, bromine, benzyloxy, trifluoromethyl or trifluoromethoxy, $R^2$ represents a group of the formula —CH$_2$—OR$^8$ or X—R, in which $R^8$ denotes hydrogen, straight-chain or branched alkyl having up to 6 carbon atoms, which is optionally substituted by hydroxyl, fluorine, chlorine or phenyl, or denotes phenyl, or denotes a group of the formula —COR$^9$, in which $R^9$ denotes straight-chain or branched alkyl having up to 6 carbon atoms, and X and R have the abovementioned meanings, $R^3$ and $R^4$ are identical or different and represent hydrogen, straight-chain or branched alkyl having up to 6 carbon atoms, phenyl or represent the group of the formula —A—R$^{10}$, in which A denotes carbonyl or sulphonyl and $R^{10}$ denotes straight-chain or branched alkyl having up to 6 carbon atoms, phenyl or trifluoromethyl or $R^3$ and $R^4$, together with the nitrogen atom, form a morpholine, piperidine or pyrrolidine ring, and $R^5$ represents straight-chain or branched alkyl having up to 8 carbon atoms, cyclopropyl, cyclopentyl or cyclohexyl and their salts.

Particularly preferred compounds of the general formula (I) are those in which

X represents a group —CH=CH—,

R represents a group of the formula

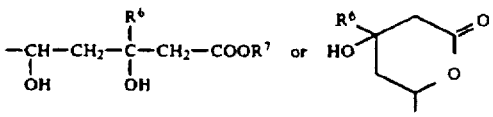

in which $R^6$ denotes hydrogen, methyl, ethyl, propyl, isopropyl, butyl, isobutyl or tert.butyl and $R^7$ denotes hydrogen, methyl, ethyl, propyl, isopropyl, butyl, isobutyl, tert.butyl or benzyl, or denotes a sodium, potassium, calcium, magnesium or ammonium ion, $R^1$ represents phenyl which is optionally monosubstituted or disubstituted by identical or different substituents from the series comprising straight-chain or branched alkyl or alkoxy in each case having up to 4 carbon atoms, benzyl, fluorine, chlorine, phenoxy or benzyloxy, $R^2$ represents a group of the formula —CH$_2$—OR$^8$ or —X—R, in which $R^8$ denotes hydrogen, straight-chain or branched alkyl having up to 4 carbon atoms or phenyl, and X and R have the abovementioned meanings, $R^3$ and $R^4$ are identical or different and represent hydrogen or straight-chain or branched alkyl having up to 4 carbon atoms or phenyl, or represent the group of the formula —A—R$^{10}$, in which A denotes carbonyl and $R^{10}$ denotes straight-chain or branched alkyl having up to 4 carbon atoms, or $R^3$ and $R^4$, together with the nitrogen atom, form a piperidine or pyrrolidine ring, $R^5$ represents straight-chain or branched alkyl having up to 6 carbon atoms or cyclopropyl, and their salts.

$R^6$ very particularly preferably represents hydrogen.

The substituted amino-pyridines of the general formula (I) according to the invention have several asymmetric carbon atoms and can therefore exist in various stereochemical forms. The invention relates both to the individual isomers and to their mixtures.

Depending on the meaning of the group X or the radical R, different stereoisomers result, which can be explained in more detail in the following:

a) If the group —X— represents a group of the formula —CH=CH—, the compounds according to the invention can exist in two stereoisomeric forms which can have the E-configuration (II) or Z-configuration (III) of the double bond:

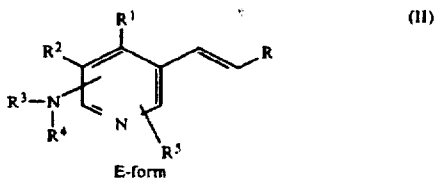

E-form

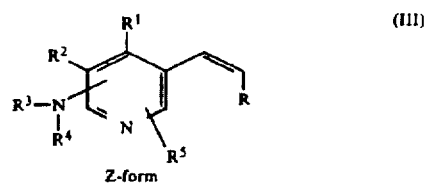

Z-form in which $R^1$, $R^2$, $R^3$, $R^4$, $R^5$ and R have the abovementioned meanings, Preferred compounds of the general formula (I) are those which have the E-configuration (II).

b) If the radical —R represents a group of the formula

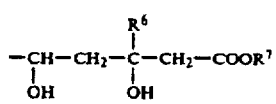

the compounds of the general formula (I) have at least two asymmetric carbon atoms, namely the two carbon atoms to which the hydroxyl groups are bonded. Depending on the relative position of these hydroxyl groups to one another, the compounds according to the invention can be present in the erythro-configuration (IV) or in the threo-configuration (V).

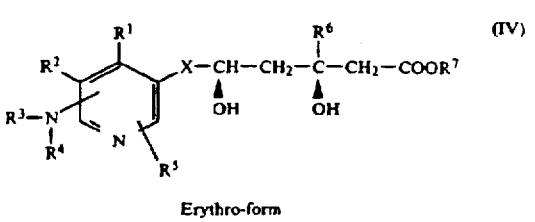

Erythro-form

-continued

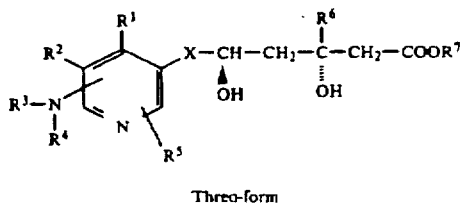

Threo-form

In each case, two enantiomers, namely the 3R,5S-isomer or the 3S,5R-isomer (erythro-form) and the 3R,5-Risomer and the 3S,5S-isomer (threo-form) in turn exist both of the compounds in the erythro- and in the threo-configuration.

The isomers in the erythro-configuration are preferred in this case, particularly preferably the 3R,5S-isomer and the 3R,5S-3S,5R-racemate.

c) If the radical —R— represents a group of the formula

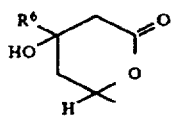

the substituted amino-pyridines have at least two asymmetric carbon atoms, namely the carbon atom to which the hydroxyl group is bonded, and the carbon atom to which the radical of the formula

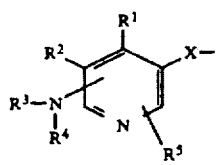

is bonded. Depending on the position of the hydroxyl group to the free valency on the lactone ring, the substituted amino-pyridines can be present as cis-lactones (VI) or as trans-lactones (VII).

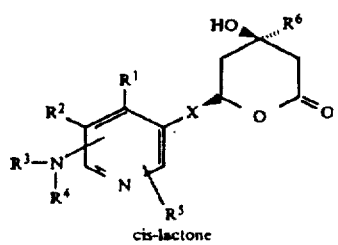
cis-lactone

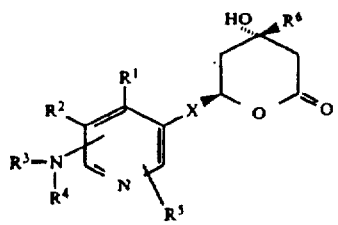

-continued
trans-lactone

In each case, two isomers, namely the 4R,6R-isomer or the 4S,6S-isomer (cis-lactone), and the 4R,6S-isomer or 4S,6R-isomer (trans-lactone) in turn exist both of the cis-lactone and the trans-lactone. Preferred isomers are the trans-lactones. The 4R,6S-isomer (trans) and the 4R,6S-4S,6R-racemates are particularly preferred in this case.

The following isomeric forms of the substituted amino-pyridines may be mentioned as examples:

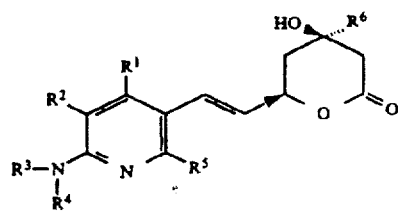

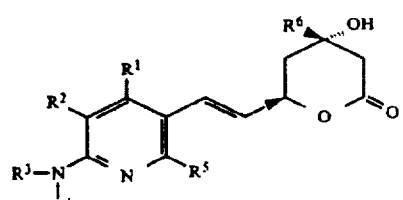

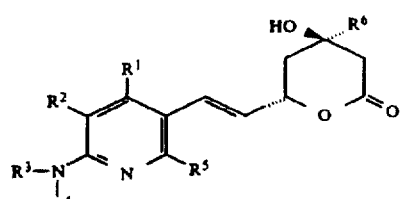

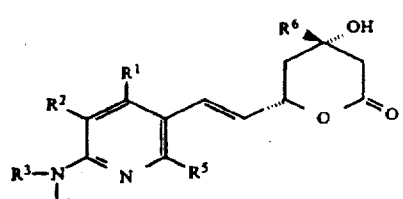

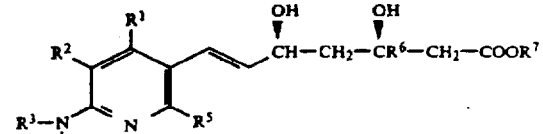

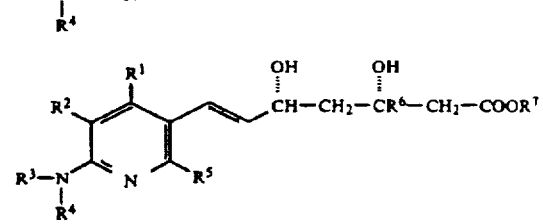

-continued

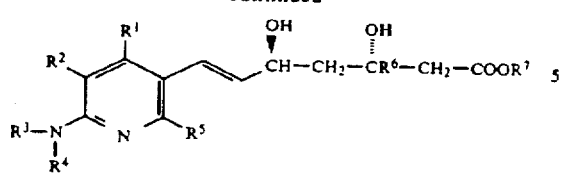

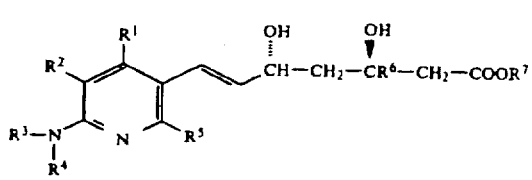

In addition, a process for the preparation of the substituted amino-pyridines of the general formula (I)

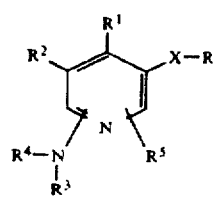 (I)

in which $R^1$, $R^2$, $R^3$, $R^4$, $R^5$, X and R have the abovementioned meanings, has been found, which is characterized in that ketones of the general formula (VIII)

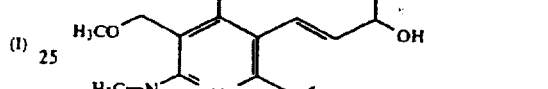 (VIII)

in which $R^1$, $R^2$, $R^3$, $R^4$ and $R^5$ have the abovementioned meanings, and $R^{11}$ represents alkyl, are reduced, in the case of the preparation of the acids, the esters are hydrolyzed, in the case of the preparation of the lactones, the carboxylic acids are cyclized, in the case of the preparation of the salts, either the esters or the lactones are hydrolyzed, in the case of the preparation of the ethylene compounds (X=—CH$_2$—CH$_2$—), the ethene compounds (X=—CH=CH—) are hydrogenated by customary methods, and, if appropriate, isomers are separated.

The process according to the invention can be illustrated by the following equation:

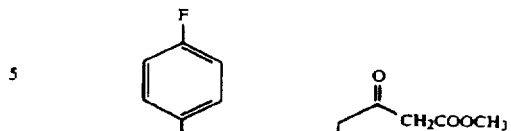

↓ Reduction

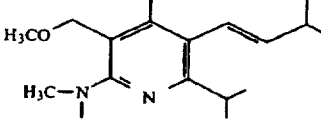

↓ Hydrolysis

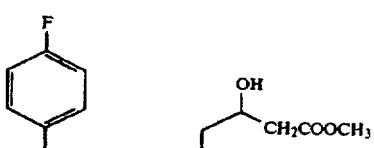

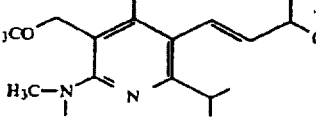

↓

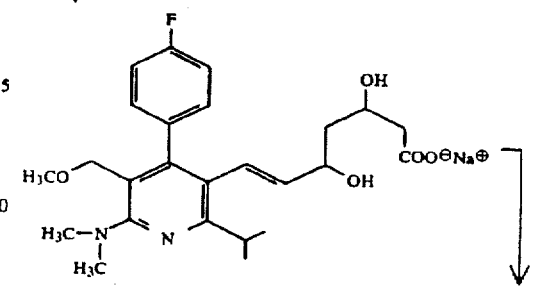

↓ Cyclization

↑

The reduction can be carried out with the customary reducing agents, preferably with those which are suitable for the reduction of ketones to hydroxyl compounds. In this case, reduction with metal hydrides or complex metal hydrides in inert solvents, if appropriate in the presence of a trialkylborane, is particularly suitable. The reduction is preferably carried out with complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride. The reduction is very particularly preferably carried out with sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is also possible to use mixtures of the solvents mentioned.

The reduction of the ketone group to the hydroxyl group is particularly preferably carried out under conditions in which the other functional groups such as, for example, the alkoxycarbonyl group, are not changed. The use of sodium borohydride as the reducing agent is particularly suitable for this purpose, in the presence of triethylborane in inert solvents such as, preferably, ethers.

The reduction is in general carried out in a temperature range from −80° C. to +30° C., preferably from −78° C. to 0° C.

The process according to the invention is in general carried out at normal pressure. However, it is also possible to carry out the process at reduced pressure or at elevated pressure (for example in a range from 0.5 to 5 bar).

In general, the reducing agent is employed in an amount from 1 to 2 moles, preferably from 1 to 1.5 moles relative to 1 mole of the ketone compound.

Under the abovementioned reaction conditions, the carbonyl group is in general reduced to the hydroxyl group without reduction of the double bond to a single bond taking place.

In order to prepare compounds of the general formula (I) in which X represents an ethylene grouping, the reduction of the ketones (III) can be carried out under those conditions under which both the carbonyl group and the double bond are reduced. Moreover, it is also possible to carry out the reduction of the carbonyl group and the reduction of the double bond in two separate steps.

The carboxylic acids in the context of the general formula (I) correspond to the formula (Ia)

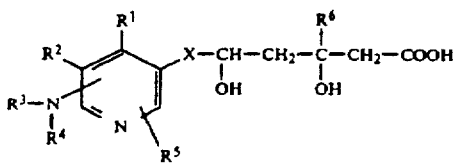

(Ia)

in which $R^1$, $R^2$, $R^3$, $R^4$, $R^5$ and $R^6$ have the abovementioned meanings.

The carboxylic acid esters in the context of the general formula (I) correspond to the formula (Ib)

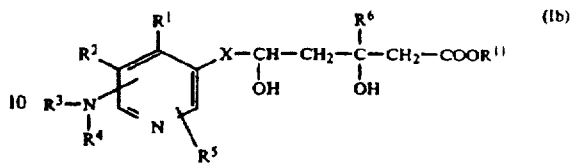

(Ib)

in which
$R^1$, $R^2$, $R^3$, $R^4$, $R^5$ and $R^6$ have the abovementioned meanings and
$R^{11}$ represents alkyl.

The salts of the compounds according to the invention in the context of the general formula (I) correspond to the formula (Ic)

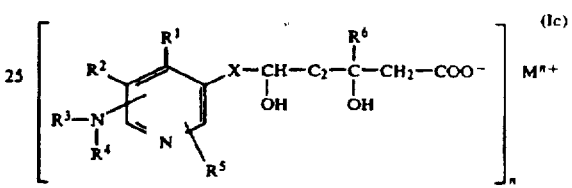

(Ic)

in which
$R^1$, $R^2$, $R^3$, $R^4$, $R^5$ and $R^6$ have the abovementioned meanings, and
$M^{n+}$ represents a cation.

The lactones in the context of the general formula (I) correspond to the formula (Id)

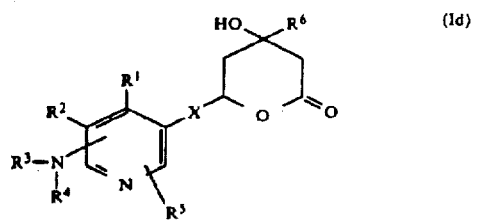

(Id)

in which
$R^1$, $R^2$, $R^3$, $R^4$, $R^5$ and $R^6$ have the abovementioned meanings.

In order to prepare the carboxylic acids of the general formula (Ia) according to the invention, the carboxylic acid esters of the general formula (Ib) or the lactones of the general formula (Id) are in general hydrolyzed by customary methods. The hydrolysis is in general carried out by treating the esters or the lactones with customary bases in inert solvents, the salts of the general formula (Ic) in general being formed first, which can then be converted into the free acids of the general formula (Ia) in a second step by treatment with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol possible to use mixtures of the solvents mentioned.

The hydrolysis is in general carried out in a temperature range of 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 moles, preferably from 1 to 1.5 moles, relative to 1 mole of the ester or the lactone. Molar amounts of the reactants are particularly preferably used.

When carrying out the reaction, the salts of the compounds (Ic) according to the invention are formed in the first step as intermediates which can be isolated. The acids (Ia) according to the invention are obtained by treating the salts (Ic) with customary inorganic acids. These preferably include mineral acids such as, for example, hydrochloric acid, hydrobromic acid, sulphuric acid or phosphoric acid. In this connection, it has proved advantageous in the preparation of the carboxylic acids (Ia) to acidify the basic reaction mixture from the hydrolysis in a second step without isolating the salts. The acids can then be isolated in a customary manner.

In order to prepare the lactones of the formula (Id) according to the invention, the carboxylic acids (Ia) according to the invention are in general cyclized by customary methods, for example by heating the corresponding acid in inert organic solvents, if appropriate in the presence of a molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons are particularly preferably used, in particular toluene, in the presence of a molecular sieve.

The cyclization is in general carried out in a temperature range of −40° C. to +200° C., preferably from −25° C. to +50° C.

The cyclization is in general carried out at normal pressure, but it is also possible to carry out the process at reduced pressure or at elevated pressure (for example in a range from 0.5 to 5 bar).

Moreover, the cyclization is also carried out in inert organic solvents, with the aid of cyclizing or dehydrating agents. Carbodiimides are preferably used in this case as dehydrating agents. The preferred carbodiimides employed are N,N'-dicyclohexylcarbodiimide paratoluenesulphonate, N-cyclohexyl-N'-[2-(N''-methylmorpholinium)ethyl]carbodiimide or N-(3-dimethylaminopropyl) -N'-ethylcarbodiimide hydrochloride.

Suitable solvents in this connection are the customary organic solvents. These preferably include ethers such as diethyl ether, tetrahydrofuran or dioxane, or chlorohydrocarbons such as methylene chloride, chloroform or carbon tetrachloride, or hydrocarbons such as benzene, toluene, xylene or mineral oil fractions. Chlorohydrocarbons such as, for example, methylene chloride, chloroform or carbon tetrachloride, or hydrocarbons such as benzene, toluene, xylene, or mineral oil fractions are particularly preferred. Chlorohydrocarbons such as, for example, methylene chloride, chloroform or carbon tetrachloride are particularly preferably employed.

The reaction is in general carried out in a temperature range of from 0° C. to +80° C., preferably from +10° C. to +50° C.

When carrying out the cyclization, it has proved advantageous to employ the cyclization method using carbodiimides as dehydrating agents.

The separation of the isomers into the stereoisomerically uniform constituents is in general carried out by customary methods such as described, for example, by E.L. Eliel, Stereochemistry of Carbon Compounds, McGraw Hill, 1962. In this connection, the separation of the isomers from the racemic lactone stage is preferred. The racemic mixture of the trans-lactones (VII) is particularly preferably converted in this case by treating either with D-(+)- or L-(−)-α-methylbenzylamine by customary methods into the diastereomeric dihydroxyamides (ie)

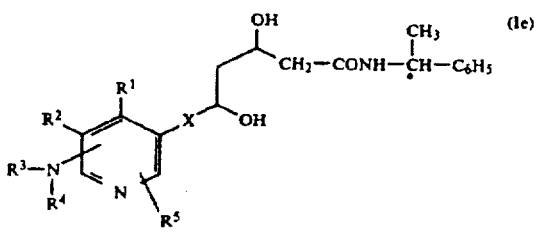

which can then be separated into the individual diastereomers by chromatography or crystallization, as is customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, gives the corresponding enantiomerically pure dihydroxy acids (Ia), which can be converted into the enantiomerically pure lactones by cyclization as described above. In general, it is true of the preparation of the compounds of the general formula (I) according to the invention in enantiomerically pure form that the configuration of the final products according to the method described above is dependent on the configuration of the starting materials.

The isomer separation is intended to be illustrated by way of example in the following scheme:

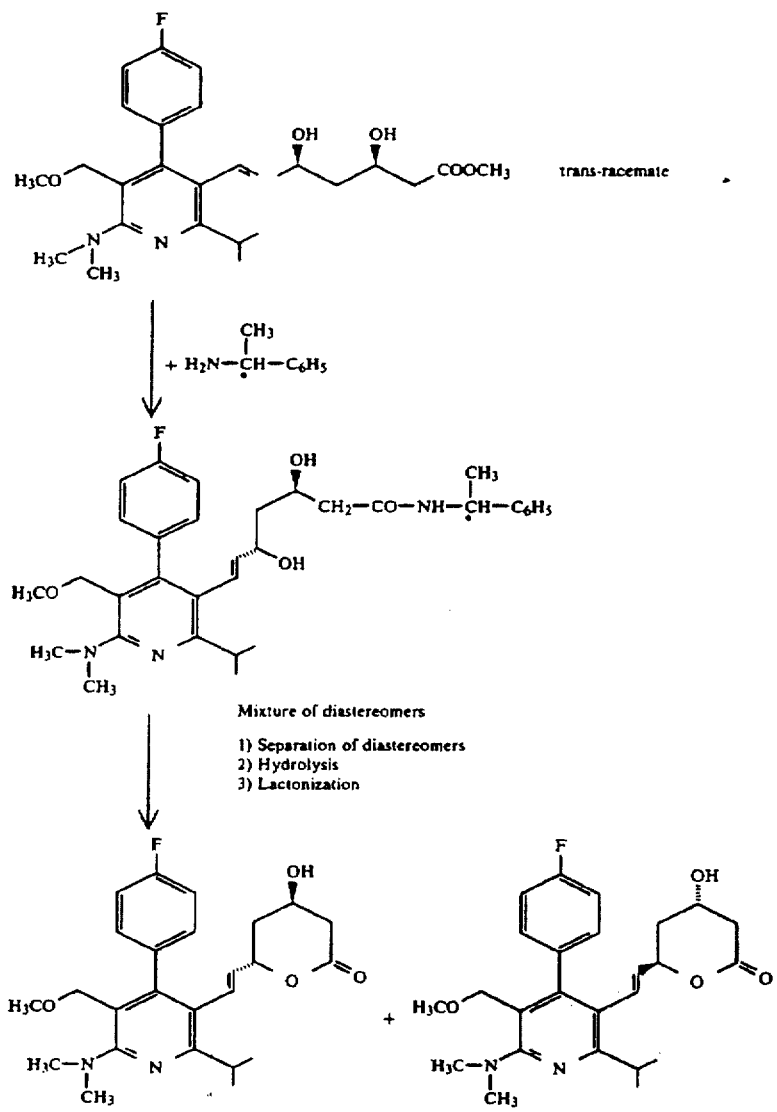

The ketones (VIII) employed as starting materials are new.

A process for the preparation of the ketones of the general formula (VIII) according to the invention

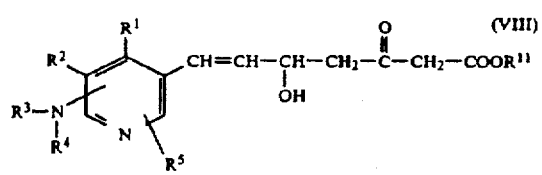

in which
R[1], R[2], R[3], R[4], R[5] and R[11] have the abovementioned meanings, has been found, which is characterized in that aldehydes of the general formula (IX)

(IX)

in which
R[1], R[2], R[3], R[4] and R[5] have the abovementioned meanings, are reacted in inert solvents with acetoacetic acid esters of the general formula (X)

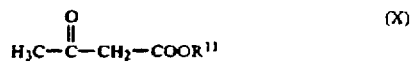

in which

R¹¹ has the abovementioned meaning, in the presence of bases.

The process according to the invention can be illustrated, for example, by the following equation:

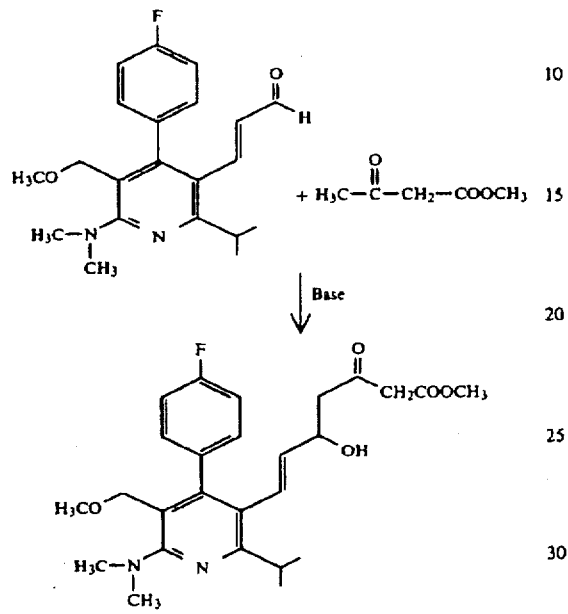

Suitable bases in this connection are the customary strongly basic compounds. These preferably include organolithium compounds such as, for example, n-butyllithium, sec.butyllithium, tert.butyllithium or phenyllithium, or amides, such as, for example, lithium diisopropylamide, sodium amide or potassium amide, or lithium hexamethyldisilylamide, or alkali metal hydrides such as sodium hydride or potassium hydride. It is also possible to employ mixtures of the bases mentioned. N-Butyllithium or sodium hydride or a mixture thereof is particularly preferably employed.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are The reaction is in general carried out in a temperature range from −80° C. to +50° C., preferably from −20° C. to room temperature.

The process is in general carried out at normal pressure, but it is also possible to carry out the process at reduced pressure or at elevated pressure, for example in a range from 0.5 to 5 bar.

When carrying out the process, the acetoacetic acid ester is in general employed in an amount from 1 to 2, preferably from 1 to 1.5 moles, relative to 1 mole of the aldehyde.

The acetoacetic acid esters of the formula (X) employed as starting materials are known or can be prepared by known methods [Beilstein's Handbuch der organischen Chemie (Beilstein's Handbook of Organic Chemistry) III, 632; 438].

Examples of acetoacetic acid esters which may be mentioned for the process according to the invention are: methyl acetoacetate, ethyl acetoacetate, propyl acetoacetate or isopropyl acetoacetate.

The preparation of the aldehydes of the general formula (IX) employed as starting materials is intended to be illustrated by way of example in the following for the compounds of the type (If) with $R^2 = -X-R$.

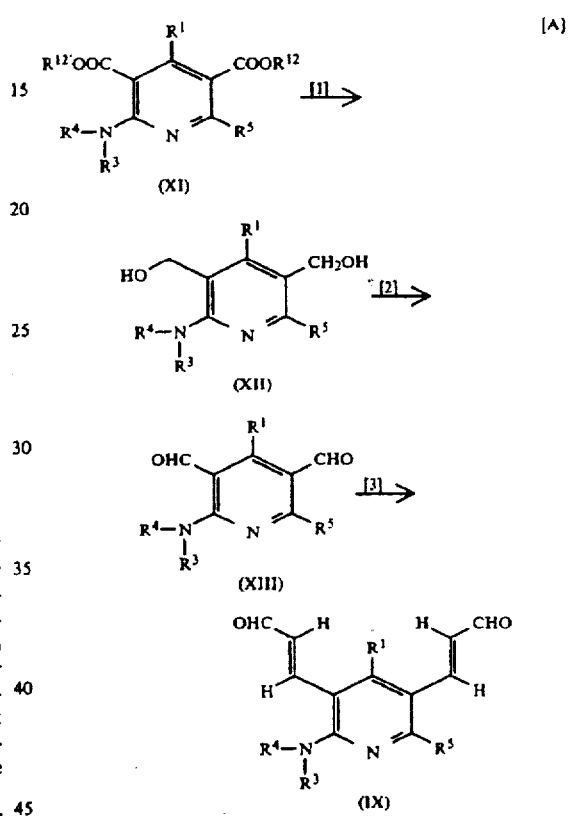

In this connection, according to scheme A, pyridines of the formula (XI), in which $R^{12}$ and $R^{12'}$ are identical or different and represent alkyl having up to 4 carbon atoms, are reduced to the hydroxymethyl compounds (XII) in a first step [1] in inert solvents such as ethers, for example diethyl ether, tetrahydrofuran or dioxane, preferably tetrahydrofuran, using metal hydrides as reducing agents, for example lithium aluminum hydride, sodium cyanoborohydride, sodium aluminum hydride, diisobutylaluminum hydride or sodium bis-(2-methoxyethoxy)-dihydroaluminate, in temperature ranges from −70° C. to +100° C., preferably from −70° C. to room temperature, or from room temperature to 70° C., depending on the reducing agent used. Reduction with lithium aluminum hydride is preferably carried out in tetrahydrofuran in a temperature range from room temperature to 80° C. The hydroxymethyl compounds (XII) are oxidized to the aldehydes (XIII) by customary methods in a second step [2]. The oxidation can be carried out, for example, with pyridinium chlorochromate, optionally in the presence of alumina, in inert solvents such as chlorohydrocarbons, preferably methylene chloride, in a temperature range from 0° C. to 60° C., preferably at room temperature, or else with trifluoroacetic acid/dimethyl sulphoxide by the customary methods of Swern oxidation. The aldehydes (XIII) are reacted to give the aldehydes (IX) in a third step [3] with diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range from −20° C. to +40° C., preferably from 5° C. to room temperature.

The pyridines of the formula (XI) employed as starting materials in this connection are in this case in general obtained according to scheme B by oxidation of dihydropyridines (XIV), which have in turn been obtained, depending on the meaning of the radical $R^2$, by variation of the corresponding functional groups. The dihydropyridines employed as starting materials in this connection are new in some cases or known and can be prepared by known methods, for example by a Knoevenagel reaction with N,N-dimethyl-ethoxycarbonyl-acetamidine hydrochloride and (E/Z)-4-carboxymethyl-5-(4-fluorophenyl)-2-methyl-pent-4-ene-3-one [compare additionally EP-A 88,276, DE-A 2,847,236]. The oxidation of the dihydropyridines (XIV) to give the pyridines (XI) can be carried out, for example, with chromic oxide in glacial acetic acid in a temperature range from −20° C. to +150° C., preferably at reflux temperature, or with 2,3-dichloro-5,6-dicyano-p-benzoquinone as the oxidizing agent in inert solvents such as chlorohydrocarbons, preferably methylene chloride in a temperature range from 0° C. to 100° C., preferably at room temperature.

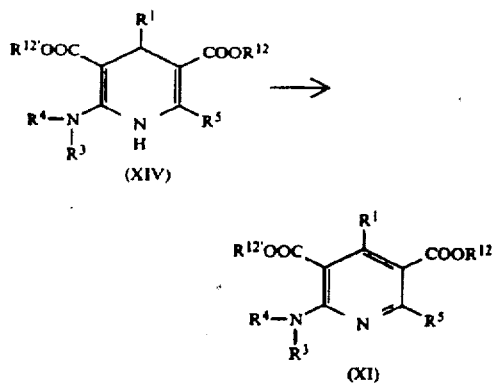

[B]

(XIV)

(XI)

In the case in which $R^2$ represents the radical —CH$_2$—OR$^8$, in which R$^8$ has the abovementioned meaning, in the starting compounds of the general formula (IX), the preparation proceeds in analogy to the steps [2] and [3] shown in scheme A. However, the compounds of the formula (XV) are prepared in a step inserted beforehand according to scheme [C].

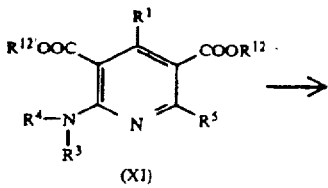

[C]

(XI)

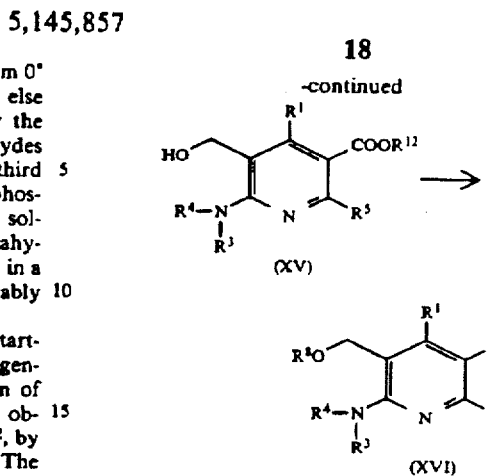

(XV)

(XVI)

The pyridines (XI), which are prepared from the corresponding dihydropyridines by oxidation as described above, can be reduced to the pyridines (XV) by suitable reducing agents, such as, for example, lithium aluminum hydride, diisobutylaluminum hydride or sodium bis-(2-methoxyethoxy)-dihydroaluminate in inert solvents, such as, for example, tetrahydrofuran.

The pyridines (XV) can be reacted to give the pyridines (XVI) by known methods, for example by reaction with an alkyl or benzyl halide in the presence of a base such as, for example, sodium hydride or, for example, by reaction with a trialkylsilyl halide or an acid halide in the presence of a base such as imidazole, pyridine or triethylamine. The hydroxyl group of the pyridines (XV) can be converted into a leaving group by known methods, for example by reaction with trifluoromethanesulphonic anhydride, thionyl chloride or methanesulphonyl chloride in the presence of a base. The leaving group can then be exchanged for nucleophiles by known methods.

The compounds of the general formula (I) according to the invention have useful pharmacological properties and can be employed in medicaments. In particular, they are inhibitors of 3-hydroxy-3-methyl-glutarylcoenzyme A (HMG-CoA) reductase and, as a result of this, inhibitors of cholesterol biosynthesis. They can therefore be employed for the treatment of hyperlipoproteinaemia, lipoproteinaemia or atherosclerosis. The active compounds according to the invention additionally cause a lowering of the cholesterol content in the blood.

The enzyme activity determination was carried out as modified by G. C. Ness et al., Archives of Biochemistry and Biophysics 197, 493-499 (1979). Male Rico rats (body weight 300-400 g) were treated with altromin powdered feed, to which 40 g of colestyramine/kg of feed had been added, for 11 days. After decapitation, the livers were removed from the animals and placed on ice. The livers were comminuted and homogenized three times in a Potter-Elvejem homogenizer in 3 volumes of 0.1M sucrose, 0.05M KCl, 0.04M $K_xH_y$ phosphate, 0.03M ethylenediaminetetraacetic acid, 0.002M dithiothreitol (SPE) buffer pH 7.2. The mixture was then centrifuged at 15,000 g for 15 minutes and the sediment was discarded. The supernatant was sedimented at 100,000 g for 75 minutes. The pellet is taken up in ⅟ volumes of SPE buffer, homogenized again and then centrifuged again at 100,000 g for 60 minutes. The pellet is taken up using a 5-fold amount of its volume of SPE buffer, homogenized and frozen and stored at −78° C. (=enzyme solution).

For testing, the test compounds (or mevinolin as a reference substance) were dissolved in dimethylformamide with the addition of 5 vol.-% of 1N NaOH and employed in the enzyme test using 10 μl in various concentrations. The test was begun after 20 minutes preincubation of the compounds with the enzyme at 37° C. The test mixture amounted to 0.380 ml and contained 4 μmol of glucose 6-phosphate, 1.1 mg of bovine serum albumin, 2.1 μmol of dithiothreitol, 0.35 μmol of NADP, 1 unit of glucose 6-phosphate dehydrogenase, 35 μmol of $K_xH_y$ phosphate pH 7.2, 20 μl of enzyme preparation and 56 nmol of 3-hydroxy-3-methyl-glutaryl coenzyme A (glutaryl-3-$^{14}$C) of 100,000 dpm.

After an incubation of 60 minutes at 37° C., the mixture was centrifuged and 600 μl of the supernatant was applied to a 0.7×4 cm column packed with a 5-chloride 100–200 mesh (anion exchanger). The column was washed with 2 ml of distilled water and 3 ml of Aquasol was added to the runnings plus washing water and counted in an LKB scintillation counter. $IC_{50}$ values were determined by intrapolation by plotting the percentage inhibition against the concentration of the compound in the test. In order to determine the relative inhibitory potency, the $IC_{50}$ value of the reference substance mevinolin was set at 1 and compared with the simultaneously determined $IC_{50}$ value of the test compound.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, in the case of the use of water as a diluent, to use, if appropriate, organic solvents as auxiliary solvents.

Examples of auxiliaries which may be mentioned are: water, non-toxic organic solvents, such as paraffins (for example mineral oil fractions), vegetable oils (for example ground nut/sesame oil), alcohols (for example: ethylalcohol, glycerol), excipients, such as, for example, ground natural minerals (for example, kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium laurylsulphate).

Administration is carried out in a customary manner, preferably orally, parenterally, perlingually or intravenously. In the case of oral administration, tablets can of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium laurylsulphate and talc can additionally be used for tabletting. In the case of aqueous suspensions, various flavor enhancers or colorants may be added to the active compounds in addition to the above-mentioned auxiliaries.

In the case of parenteral administration, solutions of the active compounds can be employed using suitable liquid excipient materials.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, depending in particular on the body weight or the manner of administration, on individual behaviour towards the medicament, the manner of its formulation and the point in time or interval at which administration takes place.

Thus, in some cases it may be sufficient to manage with less than the minimum amount previously mentioned, while in other cases the upper limit mentioned must be exceeded. In the case of the administration of relatively large amounts, it may be advisable to divide these into a number of individual doses over the course of the day.

PREPARATION EXAMPLES

EXAMPLE 1

Ethyl ethoxycarbonyl-ethaneimidate hydrochloride

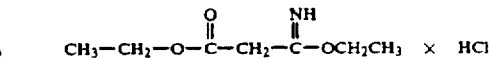

Hydrochloric acid gas is passed at 0°–10° C. into a solution of 678 g (6 mol) of ethyl cyanoacetate in 400 ml of ethanol and 3 l of ether for 7 h, the mixture is allowed to stand overnight at 25° C., and the deposited solid is filtered off with suction and dried in vacuo.

Yield: 742 g (63% of theory)

M.p.: 108°–110° C.

EXAMPLE 2

Ethyl ethoxycarbonyl-ethaneimidate

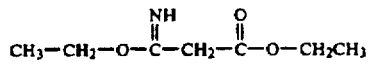

140 g (0.72 mol) of the compound from Example 1 are added in portions with stirring to a mixture of 128 g (0.93 mol) of potassium carbonate, 750 ml of ice-water and 400 ml of ether. The phases are separated, the aqueous phase is washed with ether, the ether phases are combined and dried (Na2SO4), and the solvent is removed on a rotary evaporator at 30° C. Distillation of the residue at 80°–82° C./12 mm yields 107.3 g of product.

Yield: 93.7% of theory

EXAMPLE 3

N,N-Dimethyl-ethoxycarbonyl-acetamidine hydrochloride

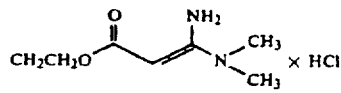

107.3 g (0.67 mol) of the compound from Example 2 and 55 g (0.67 mol) of dimethylamine hydrochloride in 300 ml of ethanol are heated under reflux overnight. The solvent is removed by distillation and the residue is triturated with acetone Yield: 94.5 g (72.5% of theory)
M.p.: 110°–112° C.

EXAMPLE 4

(E/Z)-5-(4-Fluorophenyl)-2-methyl-4-methoxycarbonyl-pent-4-en-3-one

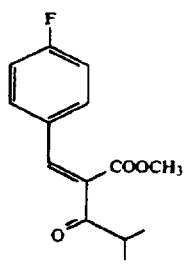

62 g (0.5 mol) of 4-fluorobenzaldehyde and 79 g (0.5 mol) of methyl isobutyrylacetate are initially introduced into 300 ml of isopropanol and a mixture of 2.81 ml (28 mmol) of piperidine and 1.66 ml (29 mmol) of acetic acid in 40 ml of isopropanol is added. The mixture is stirred at room temperature for 48 hours and concentrated in vacuo, and the residue is distilled in a high vacuum.

B.p. 4 mm: 150°–152° C.
Yield: 110.9 g (84% of theory)

EXAMPLE 5

5-Ethyl3-methyl1,4-dihydro-6-dimethylamino-4-(4-fluorophenyl)-2-isopropyl-pyridine-3,5-dicarboxylate

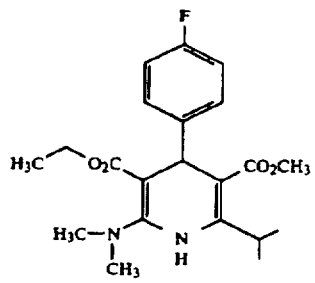

94.5 g (0.486 mol) of the compound from Example 3, 121.5 g (0.486 mol) of the compound from Example 4 and 53.4 ml (0.486 mol) of N-methyl-morpholine are stirred at 120° C. overnight, the mixture is dissolved in methylene chloride after cooling, the solution is washed with water, dried (sodium sulphate) and concentrated, and the residue is recrystallized from methanol.

Yield: 140.0 g (73.8% of theory)
M.p.: 154°–156° C.

EXAMPLE 6

5-Ethyl 3-methyl 6-dimethylamino-4-(4-fluorophenyl)-2-isopropyl-pyridine-3,5-dicarboxylate

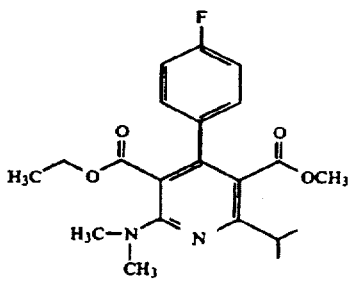

49.5 g (0.22 mol) of 2,3-dichloro-5,6-dicyano-phenzoquinone are added to a solution of 65.4 g (0.17 mol) of the compound from Example 5 in 1 l of methylene chloride at 25° C. and the mixture is stirred overnight. The precipitated solid is filtered off and washed with methylene chloride. The combined methylene chloride phases are filtered over silica gel (70–230 mesh).

Yield: 56.2 g (86% of theory)

$^1$H-NMR (CDCl$_3$): δ (ppm)=0.9 (tr, 3H); 1.25 (d, 6H); 3.0 (sept, 1H); 3.1 (s, 6H); 3.4 (s, 3H); 3.9 (q, 2H); 6.9–7.3 (m, 4H).

EXAMPLE 7

Ethyl 6-dimethylamino-4-(4-fluorophenyl)-3-hydroxymethyl-2-isopropyl-5-carboxylate

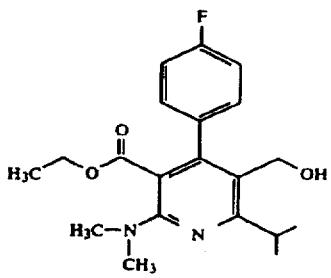

85 ml (0.29 mol) of a 3.5 molar solution of sodium bis-(2-methoxyethoxy)-dihydroaluminate in toluene are added under nitrogen to a solution of 56.2 g (0.145 mol) of the compound from Example 6 in 250 ml of tetrahydrofuran at 25° C. and the mixture is stirred overnight at 50° C. The mixture is hydrolysed cautiously with a solution of 100 g of potassium sodium tartrate in 200 ml of water, the phases are separated, the aqueous phase is washed with ether, and the combined organic phases are washed with water, dried over sodium sulphate and chromatographed on a silica gel column using petroleum ether/ethyl acetate 5:1.

Yield: 9.1 g (17.4% of theory)

¹H-NMR (CDCl₃): δ (ppm) = 0.9 (t, 3H); 1.3 (d, 6H); 3.1 (s, 6H); 3.4 (sept, 1H); 3.85 (q, 2H); 4.3 (s, 2H); 7.0–7.25 (m, 4H).

The following is obtained as a by-product:

EXAMPLE 8

3,5-Dihydroxymethyl-6-dimethylamino-4-(4-fluorophenyl)-2-isopropyl-pyridine

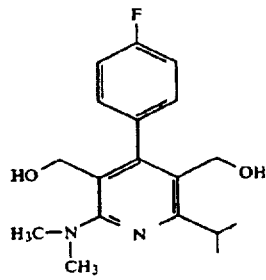

Yield: 5.6 g (12.1% of theory)
¹H-NMR (CDCl₃): δ (ppm) = 1.3 (d, 6H); 2.85 (s, 6H); 3.4 (sept, 1H); 4.3 (s, 2H); 4.4 (s, 2H); 7.1–7.2 (m, 4H).

EXAMPLE 9

6-Dimethylamino-4-(4-fluorophenyl)-2-isopropyl-pyridine-3,5-dicarbaldehyde

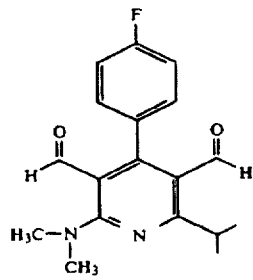

9.1 g (42.3 mmol) of pyridinium chlorochromate are added to a solution of 5.64 g (17.6 mmol) of the compound from Example 8 in 1 l of methylene chloride and the mixture is stirred at 25° C. overnight. The suspension is filtered through kieselguhr and then through silica gel.

Yield: 1.84 g (33.3% of theory)

¹H-NMR (CDCl₃): δ (ppm) = 1.25 (d, 6H); 3.2 (s, 6H); 4.1 (sept, 1H); 7.1–7.5 (m, 4H); 9.3 (s, 1H); 9.5 (s, 1H).

EXAMPLE 10

(E,E)-6-Dimethylamino-3,5-di-(prop-2-en-1-al-3-yl)-4-(4-fluorophenyl)-2-isopropyl-pyridine

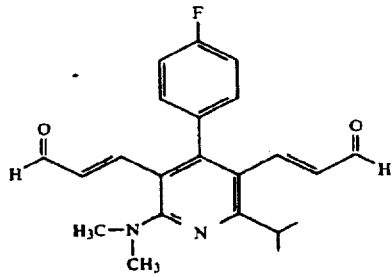

4.5 g (17.2 mmol) of diethyl 2-(cyclohexylamino)-vinylphosphonate, dissolved in 12 ml of dry tetrahydrofuran, are added dropwise under nitrogen to a suspension of 344 mg (14.3 mmol) of sodium hydride in 20 ml of dry tetrahydrofuran at −5° C. After 30 min, 1.8 g (5.7 mmol) of the compound from Example 9 in 20 ml of dry tetrahydrofuran are added dropwise at the same temperature and the mixture is heated to reflux for 30 min. After cooling to room temperature, the mixture is added to 200 ml of ice-cold water and extracted three times with 100 ml of ethyl acetate each time. The combined organic phases are washed with saturated sodium chloride solution and dried over magnesium sulphate. After concentrating in vacuo, the residue is taken up in 70 ml of toluene, a solution of 3.8 g (49 mmol) of oxalic acid dihydrate in 50 ml of water is added and the mixture is heated to reflux for 30 min. After cooling to room temperature, the phases are separated, and the organic phase is washed with saturated sodium chloride solution, dried over magnesium sulphate and concentrated in vacuo. The residue is chromatographed on a column (100 g of silica gel 70–230 meshφ3.5 cm, using methylene chloride).

Yield: 1.42 g (67.6% of theory)
¹H-NMR (CDCl₃): δ (ppm) = 1.3 (d, 6H); 3.0 (s, 6H); 3.35 (sept, 1H); 5.85 (dd, 1H); 6.1 (dd, 1H); 7.0–7.3 (m, 6H); 9.35 (m, 2H).

EXAMPLE 11

6-Dimethylamino-3,5-bis-(methyl-(E)-5-hydroxy-3-oxo-hept-6-enoat-7-yl)-4-(4-fluorophenyl)-2-isopropyl-pyridine

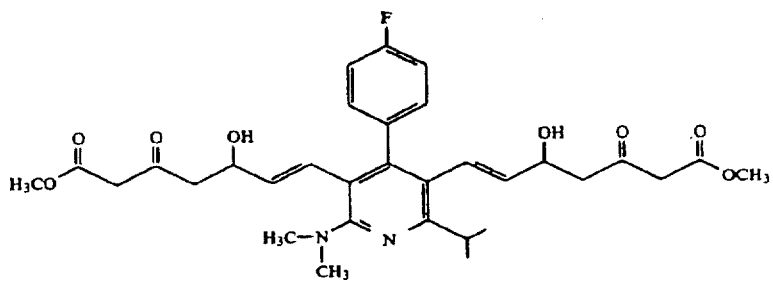

2.57 ml (23.8 mmol) of methyl acetoacetate are added dropwise under nitrogen to a suspension of 583 mg (24.3 mmol) of sodium hydride in 20 ml of dry tetrahydrofuran at −5° C. After 15 min, 17 ml (24.3 mmol) of 15% strength butyllithium in n-hexane are added dropwise at the same temperature and the mixture is subsequently stirred for 15 min. 1 39 g (3.8 mmol) of the compound from Example 10 dissolved in 20 ml of dry tetrahydrofuran are then added dropwise and the mixture is subsequently stirred at −5° C. for 30 min. 100 ml of aqueous ammonium chloride solution are added to the reaction solution and the mixture is extracted three times using 100 ml of ether each time. The combined organic phases are washed twice with saturated sodium hydrogen carbonate solution and once with saturated sodium chloride solution, dried over magnesium sulphate and concentrated in vacuo.

Crude yield: 3.04 g (>100% of theory)

EXAMPLE 12

6-Dimethylamino-3,5-bis-(methyl-erythro-(E)-3,5-dihydroxy-hept-6-enoat-7-yl)-4-(4-fluorophenyl)-2-isopropylpyridine

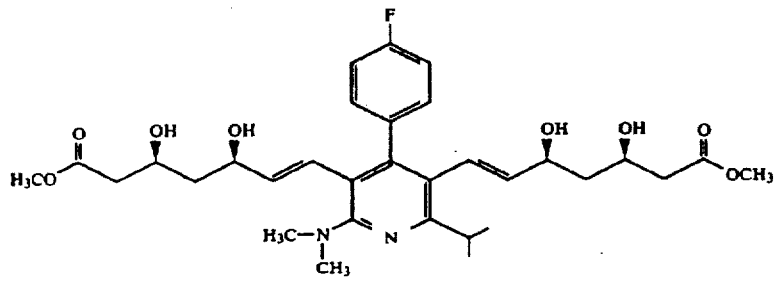

11 ml (11 mmol) of 1M triethylborane solution in tetrahydrofuran are added at room temperature to a solution of 3.0 g (5.0 mmol) of the compound from Example 1 in 80 ml of dry tetrahydrofuran, air is passed through the solution for 5 min and it is cooled to an internal temperature of −30° C. 416 mg (11 mmol) of sodium borohydride and, slowly, 19.3 ml of methanol are added, the mixture is stirred at −30° C. for 30 min and a mixture of 4 ml of 30% strength hydrogen peroxide and 70 ml of water is then added. The temperature is allowed to rise to 0° C. during the course of this and the mixture is subsequently stirred for a further 30 min. The mixture is extracted three times using 100 ml of ethyl acetate each time, and the combined organic phases are washed once each with saturated sodium hydrogen carbonate solution and saturated sodium chloride solution, dried over magnesium sulphate and concentrated in vacuo. The residue is chromatographed on a silica gel column (230–400 mesh) using ethyl acetate/petroleum ether 2:1.

Yield: 860 mg (38% of theory)

¹H-NMR (CDCl₃): δ (ppm)=1.2 (d, 6H); 1.25–1.6 (m, 4H); 2.4 (m, 4H); 2.9 (s, 6H); 3.25 (sept, 1H); 3.7 (2s, 6H); 4.1 (m, 2H); 4.3 (m, 2H); 5.2 (dd, 1H); 5.5 (dd, 1H); 6.2 (dd, 2H); 7.0 (m, 4H).

EXAMPLE 13

Methyl 6-dimethylamino-4-(4-fluorophenyl)-2-isopropyl-3-methoxymethyl-pyridine-5-carboxylate

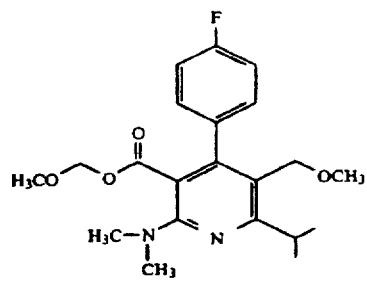

143 mg (5.96 mmol) of sodium hydride are added at 0° C. under nitrogen to a solution of 1.95 g (5.42 mmol) of the compound from Example 7 in 30 ml of tetrahydrofuran. After 30 min, 1.0 ml (16.2 mmol) of methyl iodide is added and the mixture is stirred overnight at 25° C. It is then hydrolysed cautiously using ice-water and washed three times with ether, and 1.88 g of oil are obtained after drying.

Yield: 92.5% of theory

¹H-NMR (CDCl₃): δ (ppm)=0.9 (t, 3H); 1.25 (d, 6H); 3.0 (s, 6H); 3.1 (s, 3H); 3.3 (sept, 1H); 3.85 (q, 2H); 4.0 (s, 2H); 7.0–7.2 (m, 4H).

EXAMPLE 14

6-Dimethylamino-4-(4-fluorophenyl)-5-hydroxymethyl-2-isopropyl-3-methoxymethyl-pyridine

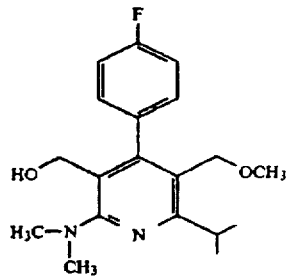

2.8 ml (9.8 mmol) of a 3.5 molar solution of sodium bis-(2-methoxyethoxy)-dihydroaluminate in toluene are added under nitrogen to a solution of 1.83 g (4.9 mmol) of the compound from Example 13 in 10 ml of dry tetrahydrofuran at 25° C. and the mixture is stirred overnight at 60° C. After cooling to 20° C., a solution of 10 g of potassium sodium tartrate in 20 ml of water is added dropwise cautiously and the mixture is extracted three times with 100 ml of ethyl acetate each time. The combined organic phases are washed once with saturated sodium chloride solution, dried over sodium sulphate and concentrated in vacuo.

Crude yield: 1.96 g (>100% of theory)

$^1$H-NMR (CDCl$_3$): δ (ppm)=1.2 (d, 6H); 2.8 (s, 6H); 3.1 (s, 3H); 3.25 (sept, 1H); 3.95 (s, 2H); 4.3 (s, 2H); 7.0-7.2 (m, 4H).

EXAMPLE 15

6-Dimethylamino-4-(4-fluorophenyl)-2-isopropyl-3-methoxymethyl-pyridine-5-carbaldehyde

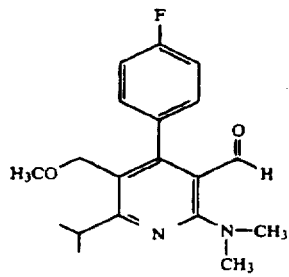

540 mg of oil are obtained from 1.86 g (5.6 mmol) of the compound from Example 14 analogously to Example 9.

Yield: 35.6% of theory $^1$H-NMR (CDCl$_3$): δ (ppm)=1.3 (d, 6H); 3.1 (s, 6H); 3.2 (s, 3H); 3.3 (sept, 1H); 4.0 (s, 2H); 7.1-7.4 (m, 4H); 9.4 (s, 1H).

EXAMPLE 16

(E)-3-[6-Dimethylamino-4-(4-fluorophenyl)-2-isopropyl-3-methoxymethyl-pyrid-5-yl]-prop-2-enal

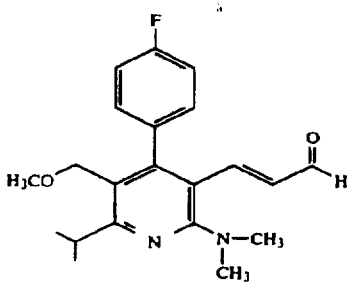

470 mg of oil are obtained from 520 mg (1.58 mmol) of the compound from Example 15 analogously to Example 10.

Yield: 83.7% of theory $^1$H-NMR (CDCl$_3$): δ (ppm)=1.3 (d, 6H); 2.9 (s, 6H); 3.15 (s, 3H); 3.3 (sept, 1H); 3.95 (s, 2H); 6.1 (dd, 1H); 7.0-7.3 (m, 5H); 9.3 (d, 1H).

EXAMPLE 17

Methyl (E)-7-[6-dimethylamino-4-(4-fluorophenyl)-2-isopropyl-3-methoxymethyl-pyrid-5-yl]-5-hydroxy-3-oxo-hept-6-enoate

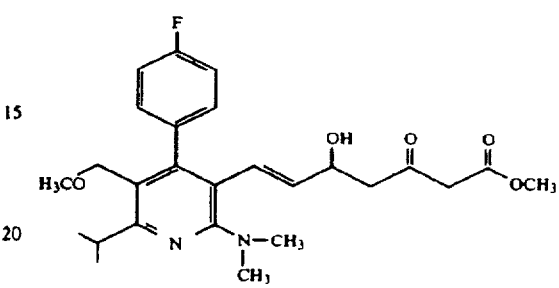

780 mg of crude product are obtained from 420 mg (1.18 mmol) of the compound from Example 16 analogously to Example 11.

Yield: >100% of theory $^1$H-NMR (CDCl$_3$): δ (ppm)=1.3 (d, 6H); 1.5 (m, 2H); 2.5 (m, 2H); 2.85 (s, 6H); 3.15 (s, 3H); 3.3 (sept, 1H); 3.7 (s, 3H); 3.95 (s, 2H); 4.45 (m, 1H); 5.45 (dd, 1H); 6.2 (d, 1H); 7.1 (m, 4H).

EXAMPLE 18

Methyl erythro-(E)-7-[dimethylamino-4-(4-fluorophenyl)-2-isopropyl-3-methoxymethyl-pyrid-5-yl]-3,5-dihydroxyhept-6-enoate

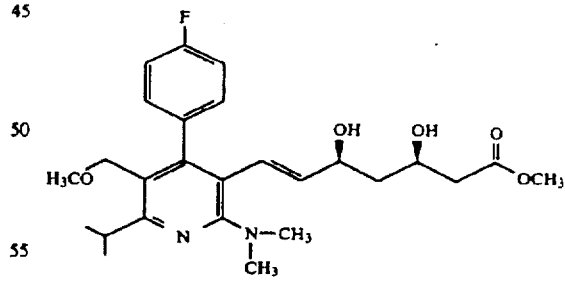

217 mg of oil are obtained from 720 mg (1.18 mmol) of the compound from Example 17 analogously to Example 12.

Yield: 38.7% of theory $^1$H-NMR (CDCl$_3$): δ (ppm)=1.25 (d, 6H); 1.5 (m, 2H); 2.4 (m, 2H); 2.9 (s, 6H); 3.1 (s, 3H); 3.3 (sept, 1H); 3.7 (s, 3H); 3.95 (s, 2H); 4.1 (m, 1H); 4.25 (m, 1H); 5.45 (dd, 1H); 6.2 (d, 1H); 7.0-7.2 (m, 4H).

EXAMPLE 19

Ethyl 3-(tert.-butyldimethylsilyloxymethyl)-6-dimethylamino-4-(4-fluorophenyl)-2-isopropyl-pyridine-5-carboxylate

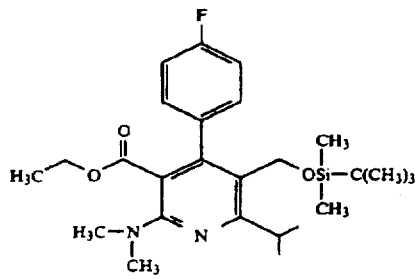

2.32 g (15.4 mmol) of tert.butyldimethylsilyl chloride, 1.9 g (28 mmol) of imidazole and 0.05 g of 4-dimethylaminopyridine are added at room temperature to a solution of 5.03 g (14 mmol) of the compound from Example 7 in 50 ml of dimethylformamide. The mixture is stirred overnight at room temperature, 200 ml of water are added and the mixture is adjusted to pH 3 with 1N hydrochloric acid. The mixture is extracted three times using 100 ml of ether each time, and the combined organic phases are washed once with saturated sodium chloride solution, dried over sodium sulphate and concentrated in vacuo.

Crude yield: 7.58 g (>100% of theory)

$^1$H-NMR (CDCl$_3$) δ (ppm)=0.0 (s, 6H); 0.8 (s, 9H); 1.25 (d, 6H); 3.0 (s, 6H); 3.3 (sept, 1H); 3.8 (q, 2H); 4.2 (s, 2H); 6.9–7.3 (m, 4H).

EXAMPLE 20

3-(tert.Butyldimethylsilyloxymethyl)-6-dimethylamino-4-(4-fluorophenyl)-5-hydroxymethyl-2-isopropyl-pyridine

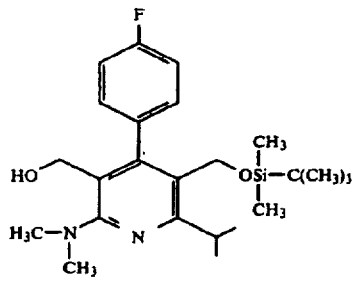

7.19 g of crude product are obtained from 7.52 g (14 mmol) of the compound from Example 19 analogously to Example 14.

Yield: >100% of theory $^1$H-NMR (CDCl$_3$): δ(ppm)=−0.1 (s, 6H); 0.8 (s, 9H); 1.3 (s, 6H); 2.85 (s, 6H); 3.35 (sept, 1H); 4.25 (s, 2H); 4.4 (s, 2H); 7.0–7.2 (m, 4H).

EXAMPLE 21

3-(tert.Butyldimethylsilyloxymethyl)-6-dimethylamino-4-(4-fluorophenyl)-2-isopropyl-5-methoxymethyl-pyridine

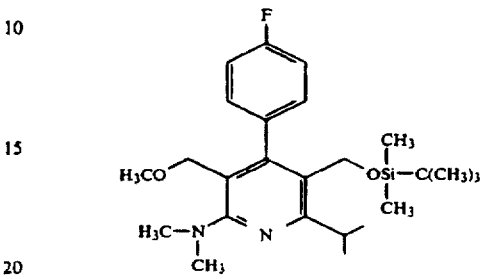

3.96 g of solid are obtained from 7.1 g (14 mmol) of the compound from Example 20 analogously to Example 13.

Yield: 63.2% of theory $^1$H-NMR (CDCl$_3$): δ (ppm)=0.0 (s, 6H); 0.9 (s, 9H); 1.35 (d, 6H); 3.1 (s, 6H); 3.15 (s, 3H); 3.45 (sept, 1H); 4.0 (s, 2H); 4.3 (s, 2H); 7.1–7.5 (m, 4H).

EXAMPLE 22

6-Dimethylamino-4-(4-fluorophenyl)-3-hydroxymethyl-2-isopropyl-5-methoxymethyl-pyridine

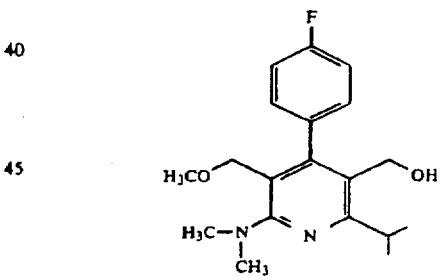

3.9 g (8.75 mmol) of the compound from Example 21 and 8.75 ml (8.75 mmol) of a 1 molar solution of tetrabutylammonium fluoride in tetrahydrofuran are stirred in 20 ml of tetrahydrofuran at 25° C. for 2.5 h. After concentrating in vacuo, the residue is dissolved in ethyl acetate, and the solution is washed 3 times with 10% strength sulphuric acid and then with saturated sodium hydrogen carbonate solution and saturated sodium chloride solution. The aqueous phase is adjusted to pH 9 and washed with methylene chloride. After drying and concentrating the combined organic phases, 6.49 g of oil are obtained.

Crude yield: >100% of theory

EXAMPLE 23

6-Dimethylamino-4-(4-fluorophenyl)-2-isopropyl-5-methoxymethyl-pyridine-3-carbaldehyde

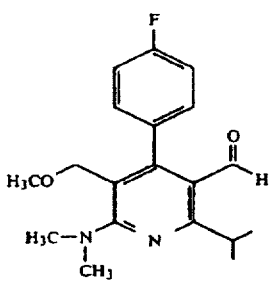

270 mg of solid are obtained from 6.49 g of the compound from Example 22 analogously to Example 9.
Yield: 9.3% of theory
¹H-NMR (CDCl₃): δ (ppm)=1.25 (d, 6H); 3.1 (s, 3H); 3.25 (s, 6H); 3.8 (s, 2H); 4.1 (sept, 1H); 7.05-7.35 (m, 4H); 9.5 (s, 1H).

EXAMPLE 24

(E)-3-[6-Dimethylamino-4-(4-fluorophenyl)-2-isopropyl-5-methoxymethyl-pyrid-3-yl]-prop-2-enal

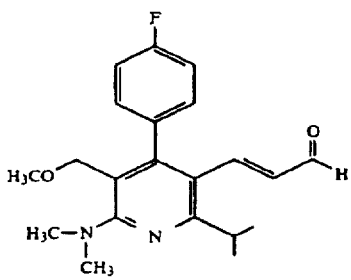

350 mg of crude product are obtained from 250 mg (0.76 mmol) of the compound from Example 23 analogously to Example 10.
Yield: >100% of theory
¹H-NMR (CDCl₃): δ (ppm)=1.3 (d, 6H); 3.1 (s, 3H); 3.15 (s, 6H); 3.35 (sept, 1H); 3.85 (s, 2H); 5.75 (dd, 1H); 7.0-7.35 (m, 5H); 9.3 (d, 1H).

EXAMPLE 25

Methyl (E)-[6-dimethylamino-4-(4-fluorophenyl)-2-isopropyl-5-methoxymethyl-pyrid-3-yl]-5-hydroxy-3-oxo-hept-6-enoate

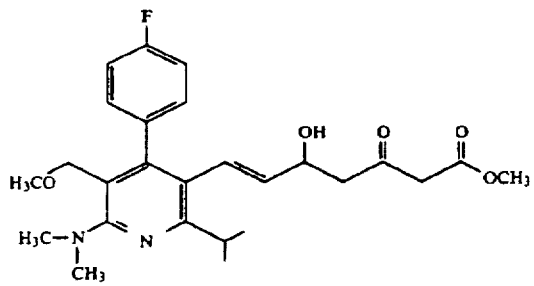

440 mg of crude product are obtained from 310 mg (0.67 mmol) of the compound from Example 24 analogously to Example 17.
Yield: >100% of theory

EXAMPLE 26

Methyl erythro-(E)-7-[dimethylamino-4-(4-fluorophenyl)-2-isopropyl-5-methoxymethyl-pyrid-5-yl]-3,5-dihydroxyhept-6-enoate

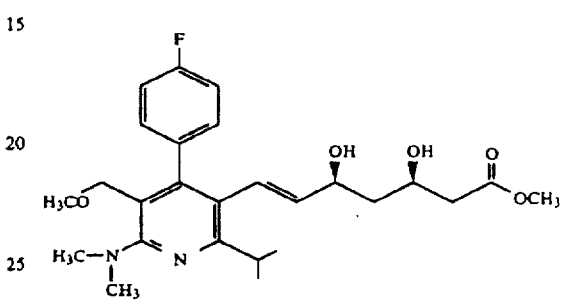

60 mg of oil are obtained from 400 mg (0.61 mmol) of the compound from Example 25 analogously to Example 12.
Yield: 20.7% of theory
¹H-NMR (CDCl₃): δ (ppm)=1.1-1.6 (m, 8H); 2.45 (m, 2H); 3.0 (s, 6H); 3.1 (s, 3H); 3.25 (sept, 1H); 3.7 (s, 3H); 3.9 (s, 2H); 4.05 (m, 1H); 4.25 (m, 1H); 5.2 (dd, 1H); 6.3 (d, 1H); 6.9-7.3 (m, 4H).

EXAMPLE 27

2-Amino-3-ethoxycarbonyl-4-(4-fluorophenyl)-5-methoxycarbonyl-1,4-dihydropyridine

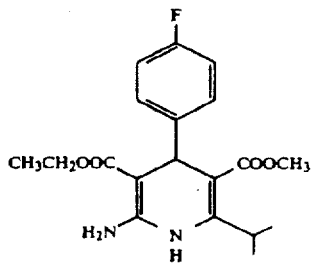

66 g (04. mol) of ethyl amidinoacetate hydrochloride (H. Meyer, F. Bossert, H. Horstmann, Liebigs Ann. Chem. 1977, 1895) are heated to reflux overnight with 100 g (0.4 mol) of the compound from Example 4 and 44 ml (0.4 mol) of triethylamine. After concentrating, the residue is filtered through 2 kg of silica gel using petroleum ether/ethyl acetate 2:1.
Yield: 109.7 g (76% of colorless crystals,
M.p. 161° C. from ether/petroleum ether).

EXAMPLE 28

2-Amino-3-ethoxycarbonyl-4-(4-fluorophenyl)
-6-isopropyl-5-methoxycarbonyl-pyridine

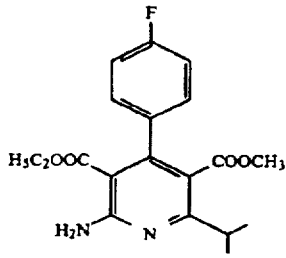

36.2 g (6.1 mol) of the compound from Example 27 are stirred at room temperature for 1 h with 22.7 g (0.1 mol) of 2,3-dichloro-5,6-dicyano-p-benzoquinone in 1 l of methylene chloride. The mixture is filtered through 1.5 kg of silica gel 230–400 mesh, washed with petroleum ether/acetic acid (2:1), the filtrate is concentrated and the residue is thoroughly stirred in ether/petroleum ether.

Yield: 31.6 g (88%) of colorless crystals of m.p. 141° C.

EXAMPLE 29

2-Amino-4-(4-fluorophenyl)-3-hydroxymethyl
-6-isopropyl-5-methoxycarbonyl-pyridine

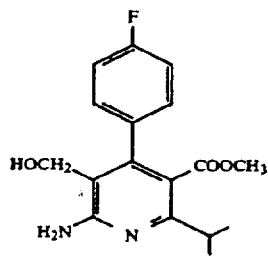

A solution of 63 g (0.175 mol) of the compound from Example 28 in 700 ml of THF is added dropwise at 25°–35° C. to 100 ml (0.35 mol) of a (3.5M) toluene Red-Al solution in 1 l of THF and the mixture is stirred at 30° C. for a further 1 h.

2 l of water are then cautiously added, the mixture is extracted twice with ethyl acetate, and the organic phases are washed with sodium chloride solution, dried and concentrated. The residue is filtered through 400 g of silica gel 230–400 mesh using petroleum ether/ethyl acetate (1:1). The concentrated filtrate gives colorless crystals of m.p. 137° C. after treating with ether/petroleum ether 45–29 (81%).

EXAMPLE 30

2-Amino-4-(4-fluorophenyl)-6-isopropyl-5-methoxycarbonyl-3-methoxymethyl-pyridine

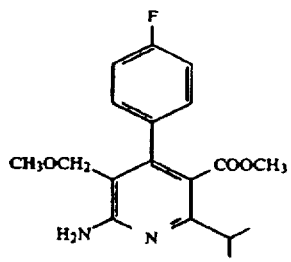

A solution of 22.2 g (70 mmol) of the compound from Example 29 in 150 ml of THF is added dropwise to a suspension of 2.3 g (77 mmol) of 80% strength sodium hydride in 150 ml of THF p.a. and the mixture is stirred at room temperature for a further 60 min.

9.95 g (70 mmol) of methyl iodide are then added dropwise and the mixture is stirred at room temperature for 3 h. The mixture is decomposed with water, extracted twice with ethyl acetate, and the organic phases are washed with saturated NaCl solution, dried over sodium sulphate and concentrated. After chromatography on 450 g of silica gel 230–400 mesh (column diameter 6 cm) using petroleum ether/ethyl acetate (2:1), 19.0 g (82%) of colorless crystals of m.p. 84° C. are obtained.

EXAMPLE 31

2-Amino-4-(4-fluorophenyl)-5-hydroxymethyl
-6-isopropyl-3-methoxymethyl-pyridine

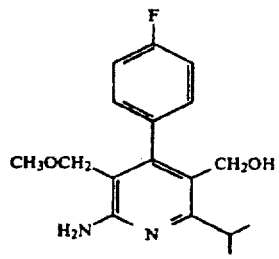

140 ml (210 mmol) of a 1.5 M solution of diisobutylaluminum hydride are added dropwise at 78° C. to −75° C. under argon to a solution of 23.1 g (70 mmol) of the compound of Example 30 in 1 l of toluene and the mixture is stirred at this temperature for 1 h. While it is allowed to warm, 40 ml of water and 50 ml of ethyl acetate are added dropwise, kieselguhr is added, filtered off with suction and washed with ethyl acetate. The aqueous phase is extracted with ethyl acetate, and the combined organic phases are washed with saturated NaCl solution and dried over sodium sulphate. The solution is concentrated to dryness and the residue is thoroughly stirred in ether.

Yield: 16.1 g (76%) of colorless crystals of m.p. 152° C.

EXAMPLE 32

2-Amino-4-(4-fluorophenyl)-5-formyl-6-isopropyl-3-methoxymethyl-pyridine

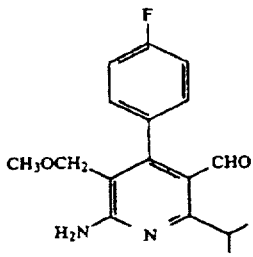

138.3 g (1.59 mol) of activated manganese dioxide are added to a suspension of 16.1 g (53 mmol) of the compound from Example 31 in 500 ml of toluene and the mixture is stirred at 75° C. for 3 h. The mixture is filtered off with suction in the hot state, and the residue is extracted by boiling with 250 ml of ethyl acetate and washed again with ethyl acetate. The combined filtrates are chromatographed on 400 g of silica gel 230-400 mesh (column diameter 6 cm) using petroleum ether-/ethyl acetate (3:1).

Yield: 9.5 g (59%) of colorless crystals of m.p. 159° C.

EXAMPLE 33

(E)-3-[2-Amino-4-(4-fluorophenyl)-6-isopropyl-3-methoxymethyl-pyrid-5-yl]prop-2-enal

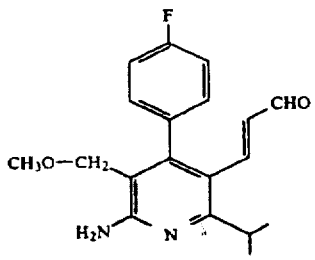

9.5 g (31.5 mmol) Of the compound from Example 32 in 100 ml of THF are added dropwise at 0°-5° C. under argon to 2.2 g (70.9 mmol) of 80% sodium hydride in 100 ml of THF, the mixture is stirred at this temperature for 10 min and heated to reflux for 1 h. Water is added, the mixture is extacted twice with ethyl acetate, and the combined organic phases are washed with saturated NaCl solution and concentrated. The residue is stirred at room temperature for 1 h in 100 ml of THF and 500 ml of 1N hydrochloric acid. The mixture is then neutralized with saturated sodium hydrogen carbonate solution, extracted twice with ethyl acetate and concentrated, and the residue is chromatographed on 400 g of silica gel using petroleum ether/ethyl acetate (3:1) to (2:4).

Yield: 2.4 g (23%) of yellowish crystals of m.p. 81° C.

EXAMPLE 34

Methyl erythro-(E)-7-[2-amino-4-(4-fluorophenyl)-6-isopropyl-3-methoxymethyl-pyrid-5-yl]-3,5-dihydroxy-hept-6-enoate

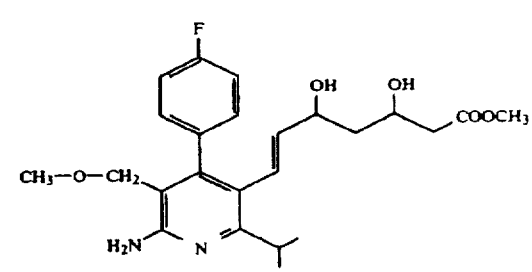

1.2 ml (11 mmol) of methyl acetoacetate are added dropwise under argon to a suspension of 0.55 g (18.3 mmol) of 80% strength sodium hydride in 20 ml of THF p.a. at 0°-5° C. and the mixture is subsequently stirred for 15 min. 13.4 ml (22 mmol) of 15% strength butyllithium in hexane are then added dropwise, the mixture is subsequently stirred at 0°-5° C. for 15 min and a solution of 1.8 g (5.5 mmol) of the compound from Example 33 in 40 ml of THF is finally added dropwise at the same temperature. After stirring at room temperature for 30 min, 2.5 ml (43.2 mmol) of acetic acid in 40 ml of water are added dropwise, the mixture is extracted twice with ethyl acetate, and the combined organic phases are washed with saturated NaCl solution, dried over sodium sulphate and concentrated to dryness.

The residue thus obtained (2.5 g) is dissolved in 35 ml of tetrahydrofuran (THF) p.a. under argon, 6.6 ml of a 1M triethylborane solution in THF are added and air is passed through the solution for 5 min. 0.25 g (6.6 mmol) of sodium borohydride are added at −78° C. and then 5.5 ml of methanol are added dropwise at −75° C.

The mixture is allowed to warm and 18.3 ml of 30% strength H$_2$O$_2$ and 40 ml of water are added during the course of this, the mixture is extracted twice with ethyl acetate, and the combined organic phases are washed with saturated NaCl solution and dried over sodium sulphate. Chromatography of the residue (50 g of silica gel 230-400 mesh, column diameter 3 cm) using petroleum ether/ethyl acetate (1:1) gives 1.1 g (45%) of yellowish oil.

$^1$H-NMR (CDCl$_3$): δ (ppm)=1.22 (m, 6H); 1.4 (m, 2H); 2.43 (m, 2H); 3.2 (s+m, 4H); 2.7 (b, 1H); 3.5 (b, 1H); 3.72 (s, 3H); 4.1 (m+s, 3H); 4.25 (m, 1H); 4.95 (b, 2H); 5.17 (dd, 1H); 6.22 (d, 1H); 7.05 (m, 4H).

EXAMPLE 35

Methyl erythro (E)-7-[2-acetylamino-4-(4-fluorophenyl)-6-isopropyl-3-methoxymethyl-pyrid-5-yl-3,5-diacetoxyhept-6-enoate

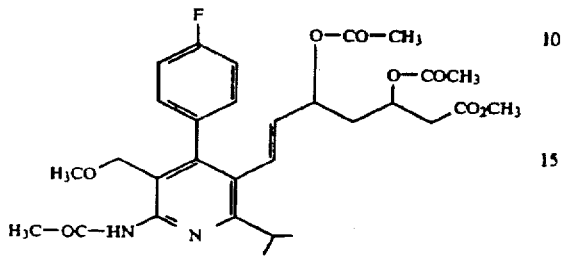

0.3 ml of pyridine, 0.25 ml of acetyl chloride and 15 mg of 4-dimethylaminopyridine are added to a solution of 260 mg (0.6 mmol) of the compound from Example 34 in 10 ml of dichloromethane and the mixture is stirred at room temperature for 1 day. Water is then added, the mixture is washed with saturated hydrogen carbonate and sodium chloride solution and concentrated, and the residue is chromatographed on 25 g of silica gel 230–400 mesh using petroleum ether/ethyl acetate (2:1) to (1:1).

Yield: 33 mg (10%) of yellowish oil
DCI-MS: 573 (M+H, 100%)

EXAMPLE 36

5-ethyl 3-methyl 1,4-dihydro-4-(4-fluorophenyl)-2-isopropyl-6-pyrrolidino-pyridine-3,5-dicarboxylate

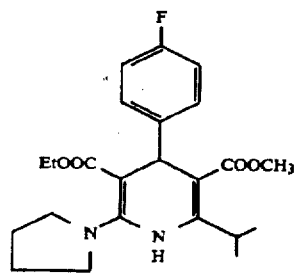

14.4 g (50 mmol) of the compound of Example 4 and 11 g (50 mmol) of ethyl 2-amino-2-pyrrolidino-prop-2-enecarboxylate hydrochloride are dissolved in 20 ml of ethanol and, after adding 6.9 ml (50 mmol) of triethylamine, the mixture is heated under reflux overnight. After cooling, the mixture is concentrated and chromatographed on silica gel (eluant ethyl acetate/petroleum ether 2:8).

Yield: 14.02 g (67.4% of theory)

EXAMPLE 37

5-Ethyl 3-methyl 4-(4-fluorophenyl)-2-isopropyl-6-pyrolidino-pyridine-3,5-dicarboxylate

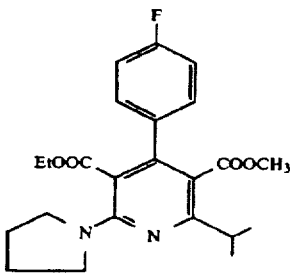

9.2 g (66.3% of theory) are obtained from 14 g of the compound from Example 36 analogously to Example 6.
$^1$H-NMR (CDCl$_3$): δ (ppm)=0.9 (t, 3H); 1.26 (d, 6H); 1.95 (m, 4H); 3.07 (sept., 1H); 3.43 (s, 3H); 3.52 (m, 4H); 3.88 (q, 2H); 6.9–7.3 (m, 4H).

EXAMPLE 38

Ethyl 4-(4-fluorophenyl)-3-hydroxymethyl-2-isopropyl-6-pyrrolidino-pyridine-5-carboxylate

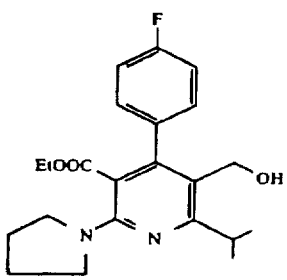

6.93 g (80.9% of theory) are obtained from 9.2 g of the compound from Example 37 analogously to Example 7.
$^1$H-NMR (CDCl$_3$): δ (ppm)=0.9 (t, 3H); 1.28 (d, 6H); 1.92 (m, 4H); 3.37 (sept., 1H); 3.51 (m, 4H); 3.85 (q, 2H); 4.31 (d, 2H); 7.0–7.3 (m, 4H).

EXAMPLE 39

Methyl erythro-(E)-7-[4-(4-fluorophenyl)-2-isopropyl-5-methoxymethyl-6-pyrrolidino-pyrid-3-yl]-3,5-dihydroxyhept-6-enoate

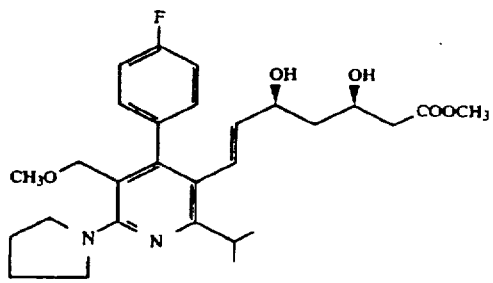

Example 39 was prepared from the compound from Example 38, in analogy to the reactions from Examples 19, 20, 21, 22, 9, 10, 11 and 12.

EXAMPLE 40

Methyl erythro-(E)-7-[4-(4-fluorophenyl)-2-isopropyl-3-methoxymethyl-6-pyrrolidino-pyrid-5-yl]-3,5-dihydroxyhept-6-enoate

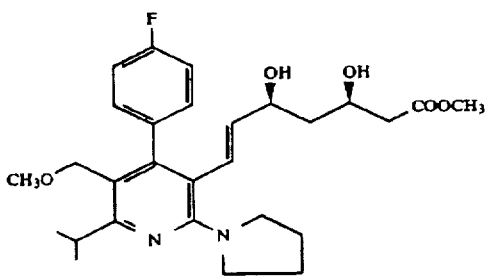

Example 40 was prepared from the compound from Example 38, in analogy to the reactions from Examples 13, 14, 9, 10, 11 and 12.

EXAMPLE 41

5-Ethyl 3-methyl 1,4-dihydro-4-(4-fluorophenyl)-2-isopropyl-6-piperidino-pyridine-3,5-dicarboxylate

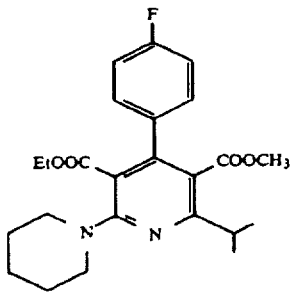

15.1 g (70% of theory) are obtained from 14.4 g (50 mmol) of the compound from Example 4 and 11.7 g (50 mmol) of ethyl 2-amino-2-piperidino-prop-2-enecarboxylate in analogy to Example 36.

EXAMPLE 42

5-Ethyl 3-methyl 4-(4-fluorophenyl)-2-isopropyl-6-piperidino-pyridine-3,5-dicarboxylate

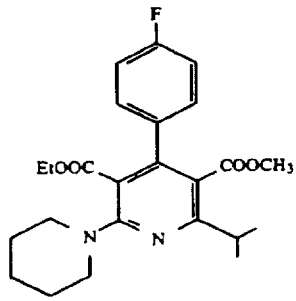

Preparation is carried out in analogy to Example 6.

$^1$H-NMR (CDCl$_3$): δ (ppm)=0.97 (t, 3H); 1.25 (d, 6H); 1.65 (m, 6H); 3.03 (sept., 1H); 3.43 (s, 3H); 3.45 (m, 4H); 3.92 (q, 2H); 6.9–7.3 (m, 4H).

EXAMPLE 43

Ethyl 4-(4-fluorophenyl)-3-hydroxymethyl-2-isopropyl-6-piperidino-pyridine-5-carboxylate

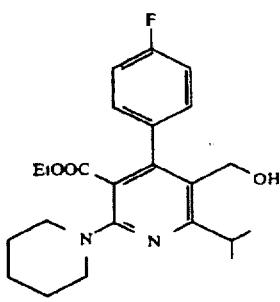

Preparation is carried out analogously to Example 7.

$^1$H-NMR (CDCl$_3$): δ (ppm)=0.98 (t, 3H); 1.28 (d, 6H); 1.62 (m, 6H); 3.42 (m, 5H); 3.90 (q, 2H); 4.32 (bs, 2H); 7.0–7.3 (m, 4H).

EXAMPLE 44

Methyl erythro-(E)-7-[4-(4-fluorophenyl)-2-isopropyl-5-methoxymethyl-6-piperidino-pyrid-3-yl]-3,5-dihydroxyhept-6-enoate

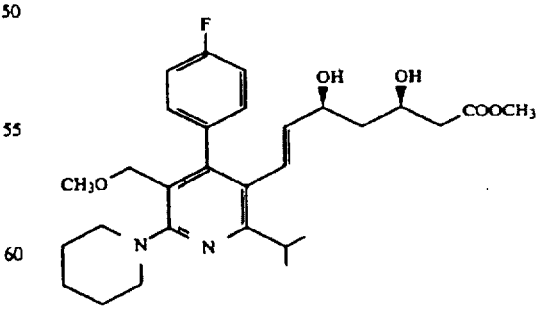

Example 44 was prepared from the compound from Example 43 in analogy to the reactions from Examples 19, 20, 21, 22, 9, 10, 11 and 12.

EXAMPLE 45

Methyl erythro-(E)-7-[4-(4-fluorophenyl)-2-isopropyl-3-methoxymethyl-6-piperidino-pyrid-5-yl]-3,5-dihydroxyhept-6-enoate

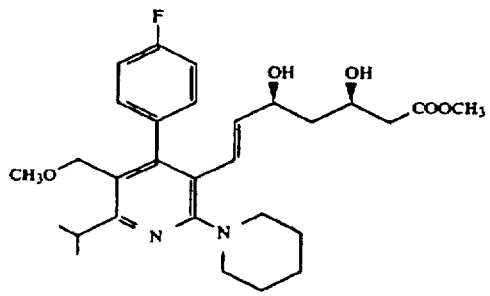

Example 45 was prepared from the compound from Example 43, in analogy to the reactions from Examples 13, 14, 9, 10, 11 and 12.

EXAMPLE 46

Methyl erythro-(E)-7-[2-dimethylamino-4-(4-fluorophenyl)-3-hydroxymethyl-6-isopropyl-pyrid-5-yl]-3,5-dihydroxy-hept-6-enoate

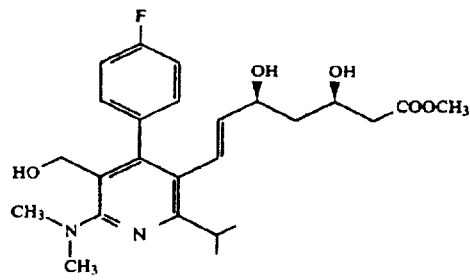

EXAMPLE 47

Methyl erythro-(E)-7-[2-cyclopropyl-6-dimethylamino-4-(4-fluorophenyl)-5-methoxymethyl-pyrid-3-yl]-3,5-dihydroxy-hept-6-enoate

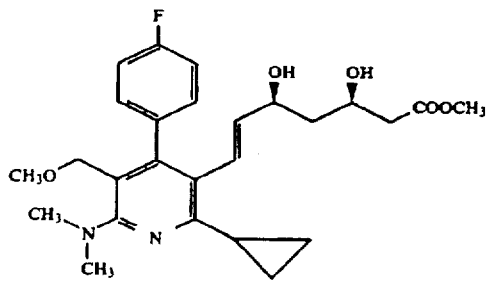

EXAMPLE 48

Methyl erythro-(E)-7-[2-cyclopropyl-6-dimethylamino-4-(4-fluorophenyl)-5-hydroxymethyl-pyrid-3-yl]-3,5-dihydroxy-hept-6-enoate

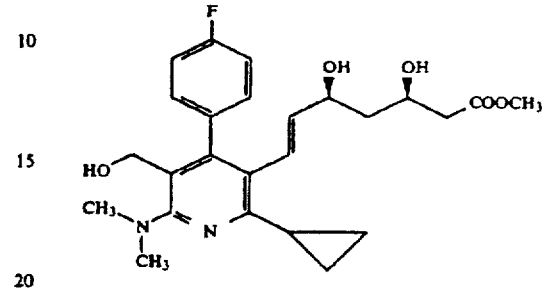

EXAMPLE 49

Methyl erythro-(E)-7-[4-(4-fluorophenyl)-3-hydroxymethyl-6-isopropyl-2-pyrrolidino-pyrid-5-yl]-3,5-dihydroxy-hept-6-enoate

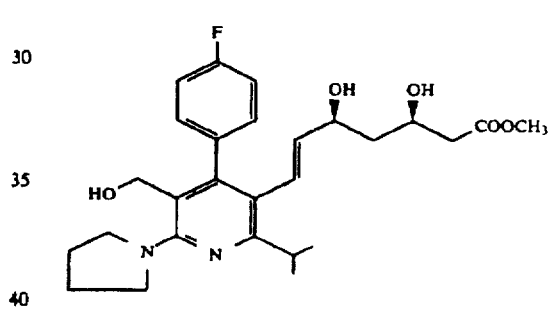

EXAMPLE 50

Methyl erythro-(E)-7-[2-cyclopropyl-4-(4-fluorophenyl)-5-hydroxymethyl-6-pyrrolidino-pyrid-3-yl]-3,5-dihydroxy-hept-6-enoate

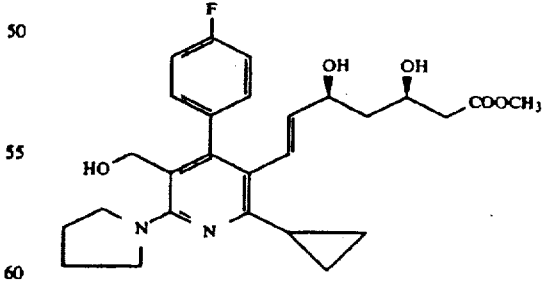

It will be appreciated that the instant specification is set forth by way of illustration and not limitation, and that various modifications and changes may be made without departing from the spirit and scope of the present invention.

What is claimed is:

1. A substituted amino-pyridine of the formula

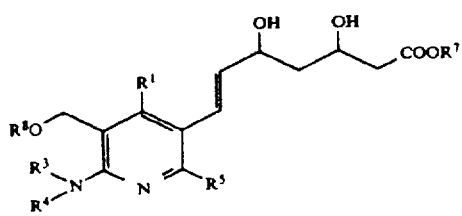

in which
R¹ represents aryl having 6 to 10 carbon atoms, which is optionally monosubstituted to tetrasubstituted by identical or different substituents from the group consisting of (a) straight-chain or branched alkyl, alkylthio, alkylsulphonyl, alkoxy or alkoxycarbonyl in each case having up to 8 carbon atoms, which may in turn be substituted by hydroxyl or phenyl, and (b) aryl, aryloxy, arylthio having 6 to 10 carbon atoms, benzyloxy, halogen, nitro, cyano, trifluoromethyl or trifluoromethoxy, R³ and R⁴ are identical or different and represent hydrogen, straight-chain or branched alkyl having up to 8 carbon atoms, phenyl or a group of the formula A—R¹⁰, in which
A denotes carbonyl or sulphonyl and
R¹⁰
denotes amino or alkoxy having up to 8 carbon atoms, straight-chain or branched alkyl having up to 8 carbon atoms or phenyl, which may in turn be substituted by hydroxyl, alkoxy having up to 8 carbon atoms or halogen, or
denotes trifluoromethyl, or
R³ and R⁴, together with the nitrogen atom, form a piperidine or pyrrolidine ring, R⁵
represents straight-chain or branched alkyl having up to 10 carbon atoms, or
represents cycloalkyl having 3 to 8 carbon atoms, R⁷
denotes hydrogen or straight-chain or branched alkyl having up to 10 carbon atoms, which may be substituted by phenyl, or
denotes aryl having 6 to 10 carbon atoms, or a sodium, potassium, calcium, magnesium or ammonium ion, and R⁸
denotes hydrogen, straight-chain or branches alkyl having up to 10 carbon atoms, which is optionally substituted by hydroxyl, halogen or phenyl, denotes aryl having 6 to 10 carbon atoms, or denotes a group of the formula —COR⁹,
in which
R⁹ denotes straight-chain or branched alkyl having up to 8 carbon atoms or phenyl,
or a pharmaceutically acceptable salt thereof.

2. A substituted amino-pyridine or salt thereof according to claim 1, in which
R¹ represents phenyl which is optionally monosubstituted to trisubstituted by identical or different substituents from the group consisting of (a) straight-chain or branched alkyl, alkoxy or alkoxycarbonyl in each case having up to 6 carbon atoms, which may in turn be substituted by phenyl, and (b) phenyl, phenoxy, fluorine, chlorine, bromine, benzyloxy or trifluoromethyl, R³ and R⁴ are identical or different and
represents hydrogen, straight-chain or branched alkyl having up to 6 carbon atoms, phenyl or
represent the group of the formula —A—R¹⁰, in which
A denotes carbonyl or sulphonyl and
R¹⁰ denotes straight-chain or branched alkyl having up to 6 carbon atoms, phenyl or trifluoromethyl, or
R³ and R⁴, together with the nitrogen atom, form a piperidine or pyrrolidine ring, and
R⁵ represents straight-chain or branched alkyl having up to 8 carbon atoms, cyclopropyl, cyclopentyl or cyclohexyl.

3. A substituted amino-pyridine or salt thereof according to claim 1, in which
R¹ represents phenyl which is optionally monosubstituted or disubstituted by identical or different substituents from the group consisting of straight-chain or branched alkyl or alkoxy in each case having up to 4 carbon atoms, benzyl, fluorine, chlorine, phenoxy and benzyloxy, R³ and R⁴ are identical or different and
represent hydrogen or straight-chain or branched alkyl having up to 4 carbon atoms or phenyl, or
represent the group of the formula —A—R¹⁰, in which
R¹⁰ denotes straight-chain or branched alkyl having up to 4 carbon atoms, or
R³ and R⁴, together with the nitrogen atom, form a piperidine or pyrrolidine ring, R⁵ represents straight-chain or branched alkyl having up to 6 carbon atoms or cyclopropyl, and R⁷
denotes hydrogen, methyl, ethyl, propyl, isopropyl, butyl, isobutyl, tert.butyl or benzyl, or
denotes a sodium, potassium, calcium, magnesium or ammonium ion.

4. A compound according to claim 1, wherein such compound is methyl erythro-(E)-7-[dimethylamino-4-(4-fluorophenyl)-2-isopropyl-3-methoxymethyl -pyrid-5-yl]-3,5-dihydroxy-hept-6-enoate of the formula

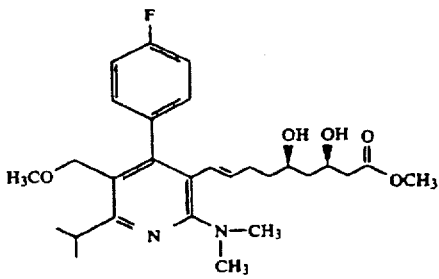

or a pharmaceutically acceptable salt thereof.

5. A compound according to claim 1, wherein such compound is methyl erythro-(E)-7-[dimethylamino-4-(4-fluorophenyl)-2-isopropyl-5-methoxymethyl -pyrid-5-yl]-3,5-dihydroxy-hept-6-enoate of the formula

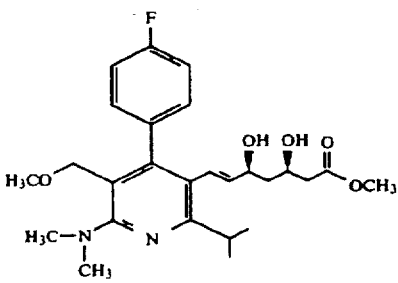

or a pharmaceutically acceptable salt thereof.

6. A compound according to claim 1, wherein such compound is methyl erythro-(E)-7-[dimethylamino-4-(4-fluorophenyl)-2-isopropyl-5-methoxymethyl-6-piperidino-pyrid-3-yl]-3,5-dihydroxy-hept-6-enoate of the formula

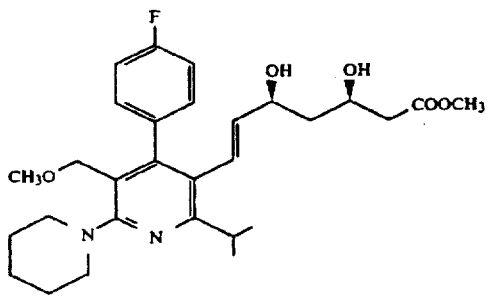

or a pharmaceutically acceptable salt thereof.

7. A compound according to claim 1, wherein such compound is methyl erythro-(E)-7-[dimethylamino-4-(4-fluorophenyl)-3-hydroxymethyl-6-isopropyl-2-pyrrolidino-pyrid-5-yl]-3,5-dihydroxy-hept-6-enoate of the formula

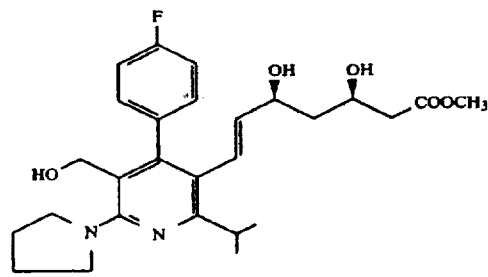

or a pharmaceutically acceptable salt thereof.

8. An MHG-CoA reductase-inhibiting composition comprising an amount effective therefor of a compound or a pharmaceutically acceptable salt according to claim 1 and a diluent.

9. The method of inhibiting HMG-CoA reductase in a patient in need thereof which comprises administering to such patient a pharmaceutically effective amount of a compound or salt thereof according to claim 1.

10. The method according to claim 9, wherein such compound is methyl erythro-(E)-7-[dimethylamino-4-(4-fluorophenyl)-2-isopropyl-3-methoxymethyl-pyrid-5-yl]-3,5-dihydroxy-hept-6-enoate, methyl erythro-(E)-7-[dimethylamino-4-(4-fluorophenyl)-2-isopropyl-5-methoxymethyl-pyrid-5-yl]-3,5-dihydroxy-hept-6-enoate, methyl erythro-(E)-7-[4-fluorophenyl)-2-isopropyl-5-methoxymethyl-6-piperidino-pyrid-3-yl]-3,5-dihydroxy-hept-6-enoate, or methyl erythro-(E)-7-[4-(4-fluorophenyl)-3-hydroxymethyl-6-isopropyl-2-pyrrolidino-pyrid-5-yl]-3,5-dihydroxy-hept-6-enoate, or salt thereof.

11. A ketone of the formula

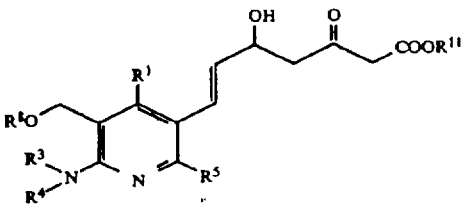

in which $R^1$ represents aryl having 6 to 10 carbon atoms, which is optionally monosubstituted to tetrasubstituted by identical or different substituents from the group consisting of (a) straight-chain or branched alkyl, alkylthio, alkylsulphonyl, alkoxy or alkoxycarbonyl in each case having up to 8 carbon atoms, which may in turn be substituted by hydroxyl or phenyl, and (b) aryl, aryloxy, arylthio having 6 to 10 carbon atoms, benzyloxy, halogen, nitro, cyano, trifluoromethyl or trifluoromethoxy, $R^2$ denotes hydrogen, straight-chain or branched alkyl having up to 10 carbon atoms, which is optionally substitute by hydroxyl, halogen or phenyl, denotes aryl having 6 to 10 carbon atoms, or denotes a group of the formula —$COR^9$, in which $R^9$ denotes straight-chain or branched alkyl having up to 8 carbon atoms or phenyl, $R^{11}$ denotes straight-chain or branched alkyl having up to 10 carbon atoms, which may be substituted by phenyl, or denotes aryl having 6 to 10 carbon atoms, $R^3$ and $R^4$ are identical or different and represent hydrogen, straight-chain or branched alkyl having up to 8 carbon atoms, phenyl or a group of the formula A—$R^{10}$, in which A denotes carbonyl or sulphonyl and $R^{10}$ denotes amino or alkoxy having up to 8 carbon atoms, straight-chain or branched alkyl having up to 8 carbon atoms or phenyl, which may in turn be substituted by hydroxyl, nitro, cyano or halogen, or denotes trifluoromethyl, or $R^3$ and $R^4$, together with the nitrogen atom, form a piperidine or pyrrolidine ring, and $R^5$ represents straight-chain or branched alkyl having up to 10 carbon atoms, or represents cycloalkyl having 3 to 8 carbon atoms.

* * * * *

UNITED STATES PATENT AND TRADEMARK OFFICE
CERTIFICATE OF CORRECTION

PATENT NO. : 5,145,857
DATED : September 8, 1992
INVENTOR(S) : Fey, et al.

Page 1 of 2

It is certified that error appears in the above-indentified patent and that said Letters Patent is hereby corrected as shown below:

Col. 44, line 58   Delete "

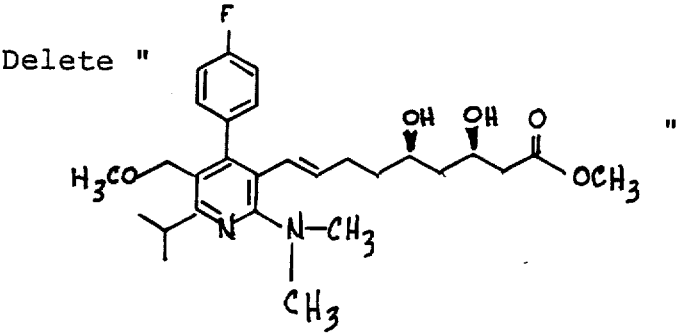

and substitute

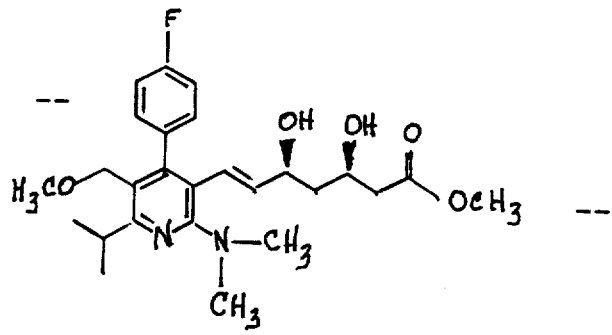

Col. 45, line 17   Delete " dimethylamino- "

UNITED STATES PATENT AND TRADEMARK OFFICE
CERTIFICATE OF CORRECTION

PATENT NO. : 5,145,857
DATED : September 8, 1992
INVENTOR(S) : Fey, et al.

It is certified that error appears in the above-indentified patent and that said Letters Patent is hereby corrected as shown below:

Col. 45, line 39    Delete " dimethylamino- "

Signed and Sealed this

Fourteenth Day of March, 1995

Attest:

BRUCE LEHMAN

Attesting Officer        Commissioner of Patents and Trademarks